United States Patent [19]

Barsa

[11] Patent Number: 4,570,640
[45] Date of Patent: Feb. 18, 1986

[54] SENSORY MONITORING APPARATUS AND METHOD

[76] Inventor: John E. Barsa, 122 Martinique, Tampa, Fla. 33606

[21] Appl. No.: 601,001

[22] Filed: Apr. 16, 1984

Related U.S. Application Data

[63] Continuation of Ser. No. 290,543, Aug. 6, 1981, abandoned.

[51] Int. Cl.$^4$ .............................................. A61B 5/05
[52] U.S. Cl. .................................................. 128/741
[58] Field of Search .................. 128/419 R, 421, 422, 128/423 R, 731, 734, 741

[56] References Cited

U.S. PATENT DOCUMENTS

| | | | |
|---|---|---|---|
| 3,513,834 | 5/1970 | Suzuki et al. | 128/731 |
| 3,810,457 | 5/1974 | Bottcher et al. | 128/741 |
| 4,064,870 | 12/1977 | Dumitrescu et al. | 128/741 |
| 4,166,452 | 9/1972 | Generales, Jr. | 128/741 |

Primary Examiner—William E. Kamm
Attorney, Agent, or Firm—O'Rourke & Harris

[57] ABSTRACT

Apparatus and method for monitoring the sensory system of a patient to enable determination of the level and depth of spinal and epidural nerve blocks, including those induced by anesthetics administered to a patient, which blocks affect the sympathetic and motor nervous systems. The anesthesia level is sequentially and repeatedly scanned at a plurality of spaced points to provide a continuous determination of the extent and depth of superficial and deep sensation and sympathetic and motor integrity. The electronic apparatus includes a stimulator that provides selective stimulation to each element of a multiple element transmitting unit the elements of which are non-invasively positioned contiguous to the skin of a patient, and a physiological response detector to detect patent responses to stimulation sensed by the elements of a multiple element sensing unit the elements of which are also non-invasively positioned contiguous to the skin of the patient. A multiple display is provided to facilitate monitoring, and an indication and/or termination of stimulation signal is provided whenever stimulation exceeds a reference level. The system and method are also shown to be usable for automatically controlling delivery of an anesthesic to a patient.

30 Claims, 20 Drawing Figures

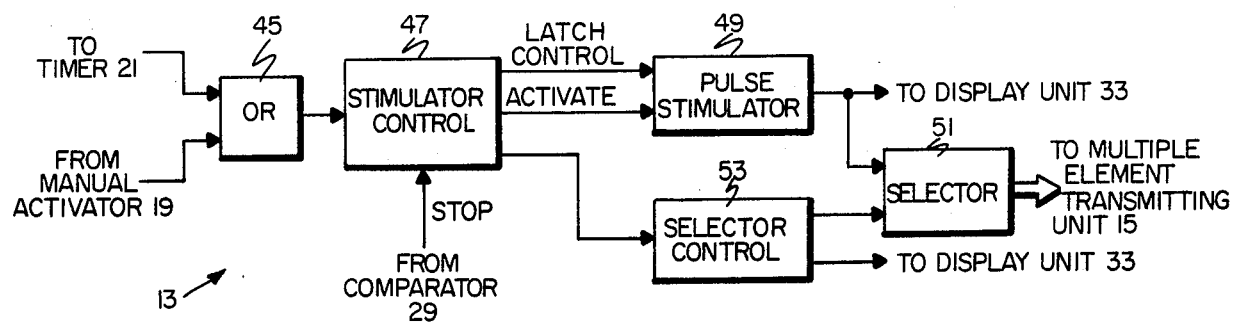
FIG. 2
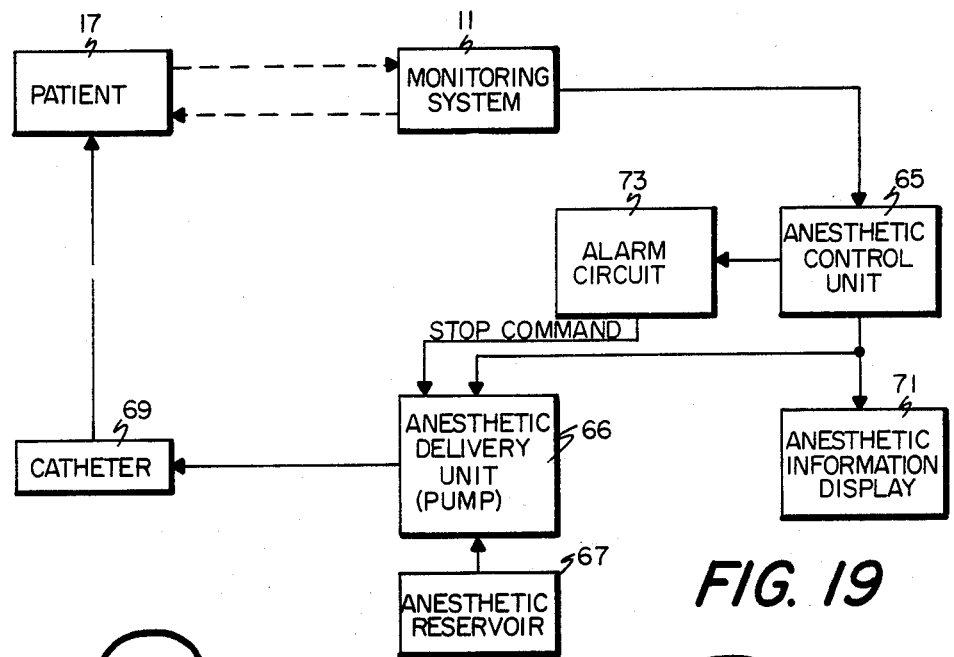
FIG. 19
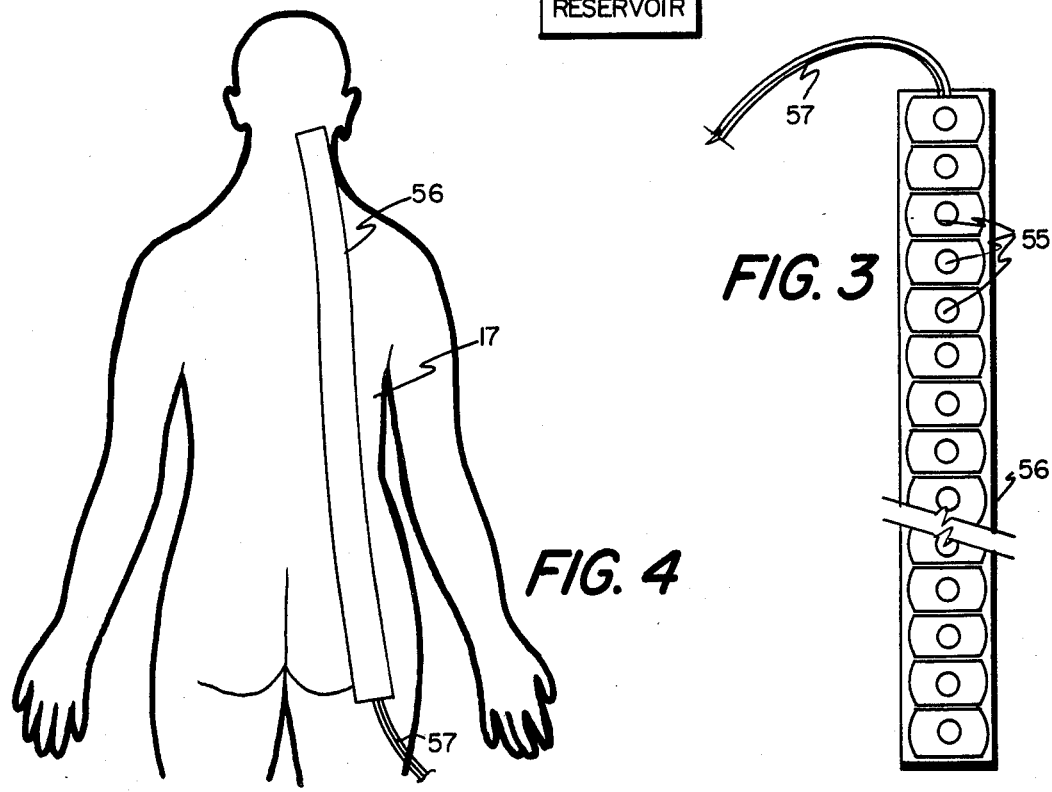
FIG. 3
FIG. 4

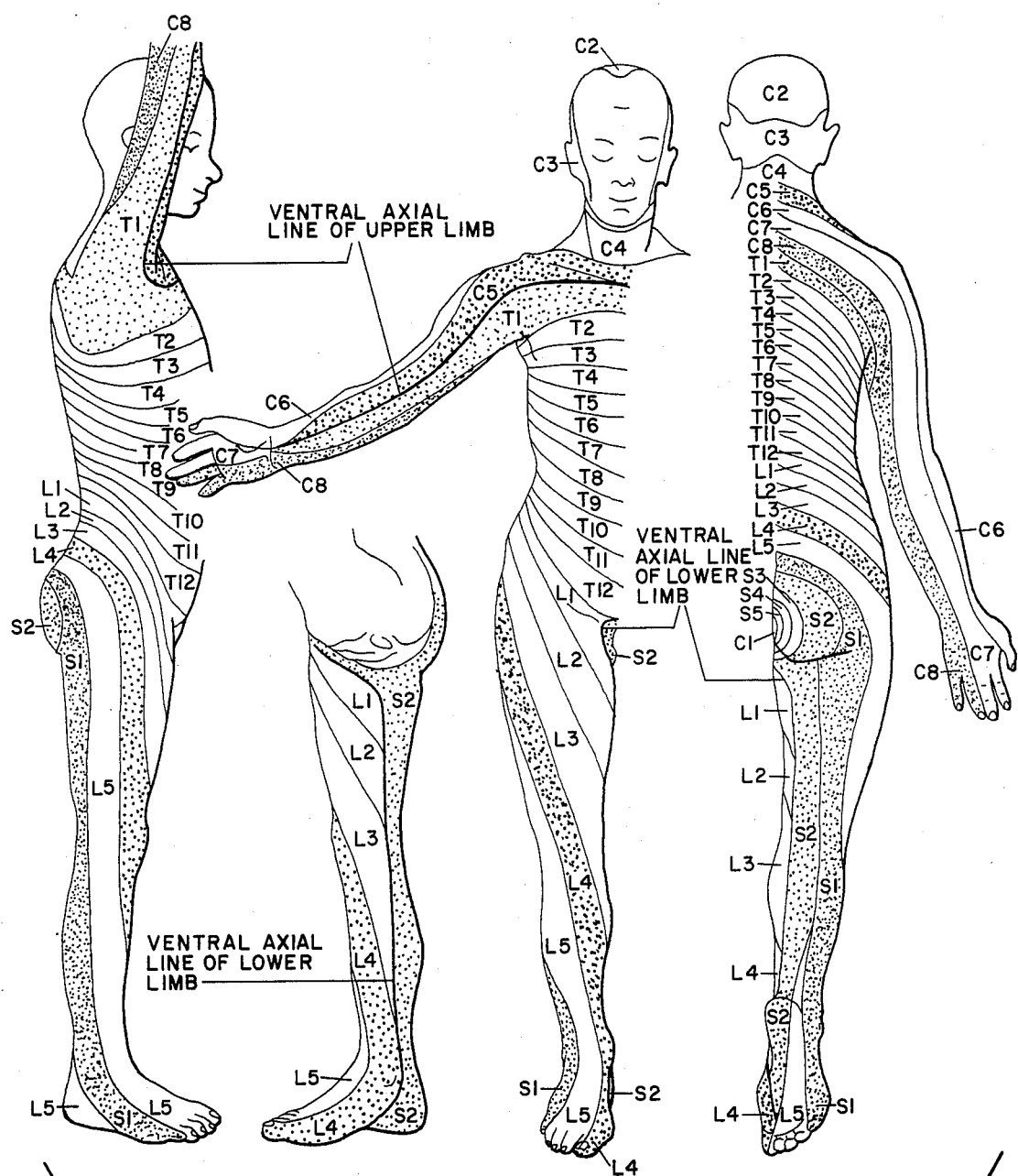
Fig_6

SENSORY MONITORING APPARATUS AND METHOD

RELATED APPLICATION

This application is a continuation of now abandoned U.S. patent application, Ser. No. 290,543, filed Aug. 6, 1981.

FIELD OF THE INVENTION

This invention relates to a sensory monitoring apparatus and method, and, more particularly, relates to apparatus and method for monitoring the sensory input system of a patient to enable determining of the level and depth of blocks of transmission of nerve impulses at the spinal cord level including those induced by an anesthetic administered to the patient.

GENERAL BACKGROUND

It is well known that spinal and epidural nerve blocks occur in humans and other animals due to a variety of causes; and such blocks can be temporary or permanent depending at least in part upon the cause.

It is likewise well known that regional anesthesia in the form of spinal and epidural nerve blocks is widely employed clinically for various surgical and non-surgical procedures to produce a temporary interruption of variable degree to various somatic sensations (which include various forms of sensations including pain sensations) and other autonomic and motor functions. Depending on the level and depth of anesthesia, spinal and eipdural nerve blocks also affect the sympathetic nervous system and can also affect the motor nervous system.

Monitoring of such nerve blocks to determine the level and/or depth of the same is obviously important, and particularly so when the block is temporarily induced.

The most common method of testing pain sensation now utilized is to strike the skin with a safety pin applying variable force. Alcohol or ether cotton swabs are also commonly used to provide information regarding the dermatominal level at which cold sensation is abolished, and this, in turn, provides information regarding the approximate level of sensory and sympathetic interruption. However, these common and simple methods are inconsistent and do not provide a monitoring system that is accurate, dependable and continuous.

The use of continuous epidural techniques is, however, desirable in situations such as long surgical procedures. This allows the injection of further doses of local anesthetic agents via an epidural catheter at intervals, or continuously, through the use of a continuous infusion apparatus. The latter case enables clinicians to maintain the continuity of a certain sensory dermatomal block level in patients under going surgery and/or for the purpose of post-operative pain relief. The use of continuous caudal and epidural anesthesia in obstetric patients for providing pain relief during labor is also relatively common. Moreover, in pain management spinal and epidural anesthesia are often used as therapeutic and diagnostic tools.

In clinical practice of regional anesthesia, it is important to regulate the level and depth of anesthetic. A low level of anesthesia could prove inadequate or risky for a particular purpose or in a particular situation. A high level and depth of anesthesia could prove dangerous as it could result in an interference with vital cardiovascular and respiratory function that could produce serious complications. Therefore, it is important to obtain accurate and continuous information regarding the depth and level of spinal and epidural anesthesia, this being vital for the patient's care.

In the area of clinical research of spinal and epidural anesthesia, such information provides a basis for a comparison, for example, between the effects of various local anesthetic agents and the resulting level and depth and duration of the anesthetic. The accuracy of the data obtained (time segment dermatome, sclerotome, sympathotome, and myotome) depends on the systems and methods available for use in monitoring the anesthetic level and depth. As used herein, time segment dermatome is defined as the spread of analgesia or sensation loss over time along the spinal segments (sacral, lumbar, thoracic, and cervical) when tested with a specific stimulus such as pin prick or surgical stimulation, time segment sympathotome is defined as the spread of sympathetic cutaneous interruption over time and along the dermatomal distribution of spinal segments (sacral, lumbar, thoracic and cervical) when tested with a specific method such as temperature changes in skin, PGR or ultrasonic skin blood flow, and time segment myotome is defined as the spread of motor block over time and along the different spinal segments (myotomal regions) when tested with a specific method such as manually examining the motor power to ultimately determine the degree, if any, of motor power loss, or through EMG measurements.

The following are some of the disadvantages relating to the existing methods that are in common use during spinal and epidural blocks:

1. The pin prick method is both inaccurate and inconsistent, since it is directly related to the force applied to the pin by the examiner. The applied force is often difficult to regulate in order to induce a quantitative and reproducible degree of sensation or pain. Different examiners may obtain different sensory block levels and depth levels testing the patient at approximately the same time;

2. The method could be unhygienic since the skin could be injured during the process of pricking. Moreover, some patients regard this as unpleasant and see it as a primitive way of testing the anesthetic depth and level;

3. During the blocking process, a situation could arise in which it becomes difficult to determine whether or not a sensory dermatomal block of sufficient depth is established. This, in part, could be due to poor cooperation by the patient as some get exhausted from continuous pricking and could eventually refuse to cooperate with the examiner. In addition, certain drugs such as tranquillizers or narcotics could modify and complicate the interpretation of the commonly used pin prick method. During the process of onset and regression of the anesthesia, areas of dermatomal hypothesia (reduced sensation) are usually developed. These areas are often difficult to quantify when compared to that of normal sensation and their development could complicate a decision as to whether or not surgery should be allowed to start. An unpleasant and risky situation could arise whereby surgery could begin based on what seemed to be acceptable evidence of sensory loss using the pin prick method, while in fact the anesthesia is not enough to counteract the surgical noxious stimulation particularly that arising from stimulation of deeper tissues below the skin level. Clinically, it is difficult to predict the exact time required to complete the block of superficial and deep sensation from that of the beginning of the onset of spinal and epidural block. The onset, progress and depths of anesthesia (sympathetic, sensory and motor block) is different at the various spinal segments. Since the pin prick method is limited in producing pain sensation compared to that produced by the surgeon's knife which elicits higher pain sensations, some clinicians prefer to use strong stimulation and also test for deep pain as well. An example is through the use of forceps pinching the skin strongly. This method, however, is not in popular use;

4. It is generally difficult and often impossible to monitor or test the anesthesia at the various dermatomal, sympathotomal and myotomal sites once surgery starts, as this could interfere with the sterility of the surgical procedure. In addition, with the patient in supine position (for example), the sacral dermatomal segments cannot be reached as these are situated in the back of the thigh and gluteal region;

5. During epidural anesthesia, and in order to maintain the sensory level of anesthetic, reinjection of local anesthetic agents through an epidural catheter is often required. Knowledge of the preinjection sensory level is important in order to regulate and determine the dosage of the anesthetic agent that could be injected further. The issue could be complicated by the fact that often the anesthetic level achieved following the start of surgery is not the final highest level as anesthesia could continue to extend to a higher level. This could result in a serious cardiovascular and respiratory complication known as total spinal or total epidural and which in turn requires emergency measures such as administration of oxygen, possible tracheal intubation, the administration of vasopressor drugs to elevate the blood pressure, intravenous fluid administration, etc.; and 6. The available methods of testing the sensory level and depth are time consuming and often do not provide the clinician with rapid and accurate information. In addition, there is no available method that could rapidly and accurately scan the sympathetic and/or motor block levels.

The sites of action of epidurally administered local anesthetics have been studied using an apparatus with a plurality of implanted electrodes, with the study being reported in an article entitled "Differential Neural Effects of Epidural Anesthetics" by Joseph F. Cusick, Joel B. Myklebust, and Stephen E. Abram, appearing in Anesthesiology, Volume 53, No. 4, pages 299-306 (October 1980).

A device and method for monitoring neuromuscular blocks present in a patient following the administration of a muscle relaxant drug which includes sensing of the movement of a patient's digital member in response to a stimulating pulse of electrical energy is shown and discussed in U.S. Pat. Nos. 4,157,087, 3,565,080 and 3,364,929.

A device and method for monitoring the degree to which the muscles of a surgical patient have been relaxed by the use of relaxant drugs which includes detecting the flexing or clenching of the fingers, due to application of an electrical stimulus, by an inflatable bladder in the patient's hand with the pressure changes being converted into electrical signals to control dispensing of the relaxant drug to the patient is shown and disclosed in U.S. Pat. No. 3,898,983.

A device and method for controlling the level of anesthesia in surgery through measurements of biocurrents is shown and described in U.S. Pat. No. 3,946,725.

An apparatus for testing the reaction time, following a stimulus, of a subject by measurement of skin resistance to make possible evaluation of the dosage of drugs affecting the central nervous system which may be safely given to particular subjects is shown and described in U.S. Pat. No. 3,468,302.

Apparatus and methods for applying electrical signals to a patient by use of a plurality of electrodes that are sequentially energized are shown and described in U.S. Pat. Nos. 4,166,452, 4,078,553 and 3,646,940.

SUMMARY OF THE INVENTION

This invention provides apparatus and method for monitoring the sensory system of a patient to enable determining of the level and depth of spinal and epidural nerve blocks affecting the sympathetic and motor nervous system and is particularly useful where such blocks have been temporarily induced by anesthesia administered to a patient. Preselected patient areas are sequentially and repeatedly scanned to provide a continuous determination to be made of the extent and depth of superficial and deep sensations and sympathetic and motor integrity.

It is therefore an object of this invention to provide a novel apparatus and method for monitoring the sensory system of a patient.

It is another object of this invention to provide a novel apparatus and method to enable determining of the level and depth of spinal and epidural nerve blocks affecting the sympathetic and motor nervous system of a patient.

It is still another object of this invention to provide a novel apparatus and method for determining the level and depth of anesthesia administered to a patient.

It is still another object of this invention to provide a novel apparatus and method for sequentially and repeatedly scanning preselected areas of a patient and determining therefrom the extent and depth of superficial and deep sensations and sympathetic and motor integrity.

With these and other objects in view, which will become apparent to one skilled in the art as the description proceeds, this invention resides in the novel construction, combination, arrangement of parts, and method substantially as hereinafter described, and more particularly defined by the appended claims, it being understood that such changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised fo the practical application of the principles thereof, and in which:

FIG. 2 is a block diagram of the selective element stimulator as shown in FIG. 1;

FIG. 3 is a perspective view of a typical arrangement of electrodes for use as multiple element transmitting and sensing units;

FIG. 4 is a perspective view showing a typical positioning arrangement for the electrode arrangement as shown in FIG. 3;

FIG. 6 is a series of partial sketches illustrating the dermatomes of a human body;

FIG. 19 is a block diagram of the monitoring apparatus used in conjunction with an anesthetic delivery system.

DESCRIPTION OF THE HUMAN NERVOUS SYSTEM AND THE EFFECTS OF PATHWAY INTERRUPTIONS

Figure 1:
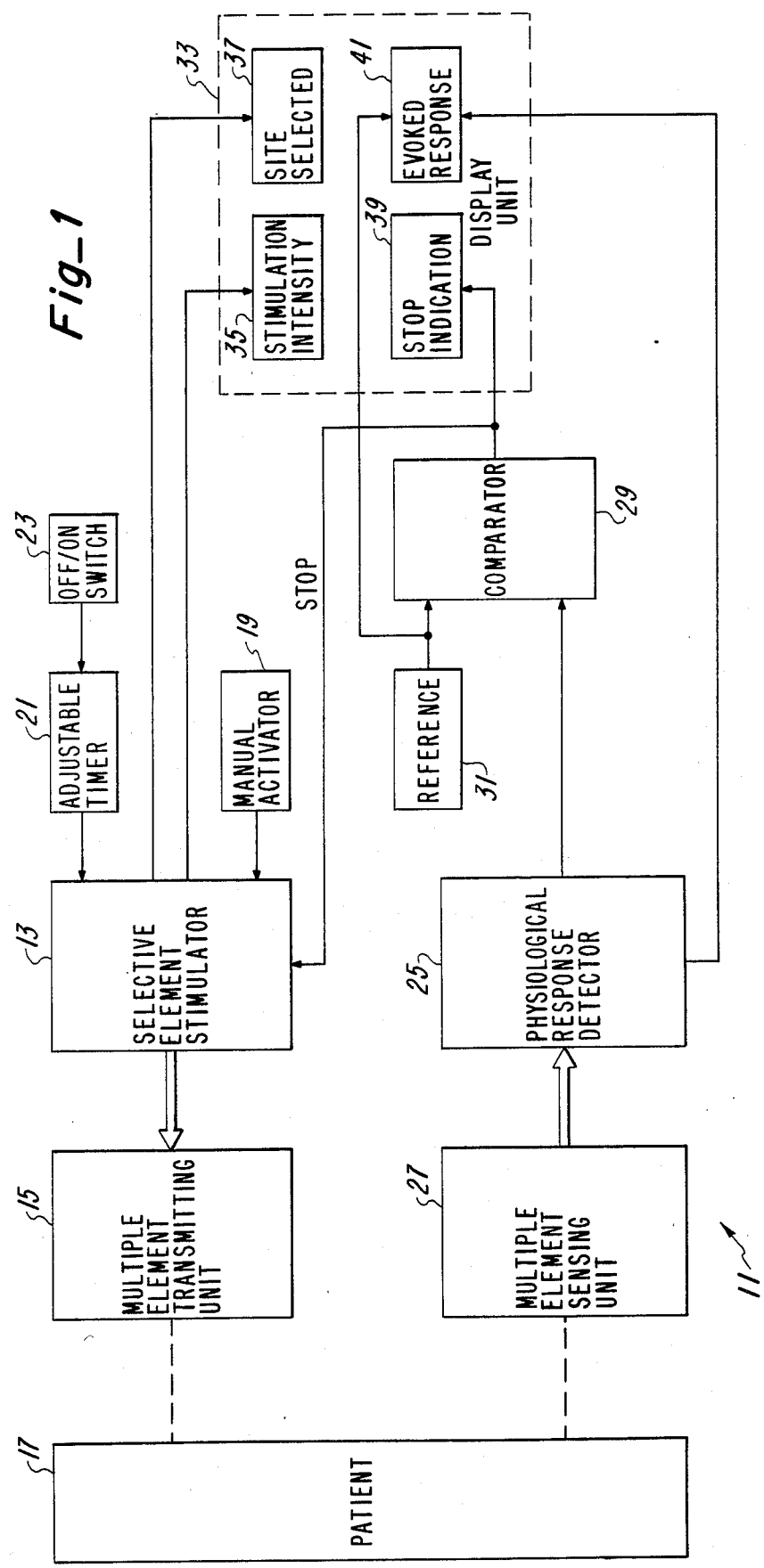
FIG. 1 is a block diagram of the monitoring apparatus of this invention.

The human nervous system is a unique complex system as it controls a vast number of body interactions. It is closely linked with the endocrine glands as both systems control the functions of the entire body. Basically, the human nervous system receives much information from different sensory organs and then proceeds to integrate all of the received information to determine the response to be made by the body.

In general, the nervous system has two divisions, the central nervous system (CNS) consisting of the brain and the spinal cord, and the peripheral nervous system (PNS) consisting of the cranial and spinal nerves and their associated nerve ganglia, the autonomic nerves and their associated ganglia, and the neuro receptors and effectors.

The brain and the spinal cord are composed of a large number of nerve cells and their processes which are supported by specialized tissue called neuraglia (the nerve cell and all its processes is called the neuron, while the long processes of a nerve is called the axon, or nerve fiber). The peripheral nervous system consists of twelve pairs of cranial nerves that leave the brain and pass through the foramina in the skull, and thirty-one pairs of spinal nerves that leave the spinal cord through the intervertebral foramina in the vertebral column.

The input of the human nervous system includes the somatic sensory division and the autonomic input division while the output includes the somatic motor division and the autonomic output division.

The spinal nerves transmit the input and output of the nervous system, and are named according to the region of the vertebral column with which they are associated. There are eight cervical spinal nerves (even though there are only seven cervical vertebrae), twelve throacic spinal nerves, five lumbar spinal nerves, five sacral spinal nerves, and one coccygeal spinal nerve (even though there are four coccygeal vertebrae).

Each spinal nerve is connected to the spinal cord by two roots, the anterior root and the posterior root. Essentially, the anterior root consists of nerve fibers, called efferent fibers, that carry away nerve impulses from the central nervous system.

The fibers in the posterior root are those which carry information about sensation of touch, pain, temperature, and vibration, so that these fibers carry impulses to the central nervous system and therefore are called the afferent fibers. The cell body of these nerve fibers are situated in a swelling on the posterior root called the posterior root ganglion.

Along the vertebral column and at each intervertebral foramen, the anterior and posterior root unite together to form a spinal nerve and at this point the efferent and the afferent nerve fibers are mixed together, the efferent being the motor fibers and the afferent being the sensory fibers.

As the spinal nerves emerge from the intervertebral foramina, they divide into two divisions, the anterior ramus and the posterior ramus. The anterior ramus continues anteriorly to supply the muscles and the skin over and through lateral parts of the body and all the muscles and overlying skin of the upper and lower limbs, as shown in FIG. 6 of the drawings. The posterior ramus passes posteriorly around the vertebral column to supply the muscle and the skin of the back, as also shown in FIG. 6 of the drawings.

In the trunk, all the muscles of the sacro-spinalis group that lie deep to the throaco-lumbar fascia (and no others) are supplied segmentally by the posterior primary rami of the spinal nerves. In the neck, splenious and all the muscles deep to it are similarly supplied. The cutanious distribution of the posterior primary rami extend further out than the extensor muscles, almost to the posterior axillary lines.

With respect to the rami, each posterior primary ramus divides into a medial and lateral branch (where both branches of all the posterior primary rami supply muscle) but only one branch (either medial or lateral) reaches the skin. However, C-1 (as shown in FIG. 6) has no cutaneous branch and the posterior primary rami of the lower two nerves in the cervical and lumbar region of the cord likewise do not reach the skin (all twelve thoracic and five sacral nerves do, however, reach the skin). In the upper half of the body, the medial branches, and in the lower half, the lateral branches of the posterior primary rami, provide the cutaneous branches, and no posterior primary ramus ever supplies skin or muscle of a limb in the human body.

The anterior primary rami supply the skin at the sides and front of the neck and the body. In the neck, only C-2, C-3 and C-4 (as shown in FIG. 6) take part by branching from the cervical plexus. The skin of C-5, C-6, C-7, C-8 and T-1 (as shown in FIG. 6) clothes the upper limb, innervated via the brachial plexus from these segments. In the trunk, the skin is supplied in strips or zones in regular sequence from T2 to L1 inclusive (as shown in FIG. 6). The intercostal nerves have each lateral branch to supply the side and anterior branch to supply the front of the body wall. The lower six thoracic nerves pass beyond the costal margin obliquely downward to supply the skin of the abdominal wall. Each nerve throughout the whole of its course supplies a strip of skin that overlies it. On the body wall, adjacent dermatomes overlap to some extent. While each spinal nerve contains a mixture of sensory and motor nerve fibers, the lateral branch and anterior terminal branch of the intercostal nerve contain sensory fibers only.

The dermatome is defined as an area of skin that is supplied by a single segment of the spinal cord (the sympathotome is defined as an area of skin supplied by a certain spinal sympathetic segmental innervation). The dermatomal distribution of the human body as described by Keegan, Grant's Atlas of Anatomy (1972) (as shown in FIG. 6) has been adopted herein. The origin of the upper and lower limbs (the anterior rami) joins together to form a nerve plexus. At the root of the arm, these are termed the cervical and brachial plexus, and at the root of the leg these are termed the lumbar and sacral plexus. It is important to realize that the classic division of the nervous system, the central nervous system, and the peripheral one is purely artificial and one of a descriptive convenience, since the process of neuron passes freely between the two.

The somatic sensory system transmits sensory information from the whole body including the deep structure. This information enters the nervous system through the spinal nerves and conducted to the spinal cord and to the higher centers. The somatic sensation can be classified into:

1. The mechano-receptors somatic sensation. This form of sensation responds to physical stimuli that causes mechanical displacement of one or more of the tissues. Touch stimuli that causes displacement, movement of the limbs and the body, pressure against the surface of the body, sound waves, tension in the muscles and tendons, body acceleration, and stretch of arterial wall by increasing flow. All these forms of mechano-receptors are received via receptors. These sensory receptors vary histologically according to their function and sensory mediation;

2. The thermoreceptive sensation. This form of sensation detects heat and cold sensation and the receptors are classified accordingly into two types—cold receptors and warm receptors. Some of these receptors are specialized forms of nerve endings and some are very complicated sensory end organs; and 3. Pain sensation. This is activated by numerous factors including sources that damage the tissue. The noxious stimulus could be extreme cold or hot sensation which produces pain, or any other form of tissue damage or irritation.

All sensory information from the somatic segment of the body enters the spinal cord through the posterior root. Once entering the cord, the nerve fibers separate into medial and laterial divisions. The medial fibers immediately enter the dorsal column of the spinal cord and ascend to the higher centers in the brain, while the lateral fibers travel upward for one to six or seven segments and downward for one to two segments and then synapse with the dorsal forn cell that give rise to the ventrical and lateral column of the spinal cord.

This separation of the fiber at the dorsal root represents a separation of the pathway for transmission of sensor impulses and therefore produces two systems:

1. The dorsal column system. This is the pathway of the dorsal column and conveys: touch sensation that requires a high degree of localization; phasic sensation such as vibratory sensation; kinesthetic sensation; muscle sensation and pressure sensation; and 2. The spinothalamic system. This is the pathway of the spinothalamic tract and conveys: pain; thermal sensation, both warm and cold sensation; touch sensation (crude) capable of less localizing ability; pressure sensation (crude) in nature; itch and tickle sensation; and sexual sensation.

With respect to segmental innervation of the skeletal muscles, the majority of the muscles, especially those of the extremities are innervated by two or three and occasionally even four ventral roots. Therefore, injury to a single ventral root may only weaken a muscle or have no apparent effect.

The anterior primary rami supplies the flexor muscle segmentally by separate branches from each nerve. The anterior rami of the twelve thoracic nerves and L1 (see FIG. 6) supply the muscles of the body wall segmentally. Each intercostal nerve supplies the muscles of each intercostal space and the lower six nerves pass beyond the costal margin to supply the muscle of the anterior abdominal wall. The first lumbar nerve ileohypogastric and ileoinguinal nerve is the lowest spinal nerve that supplies the anterior abdominal wall. The muscle just below L1 is no longer on the body wall. This has migrated into the side to become specialized into the quadraceps and adductor group of muscle (femoral and obturator nerves).

The myotome refers to that portion of the voluntary striated muscle of the body that is supplied by a given spinal nerve. The myotomes of different regions of the human body are as follows (see FIG. 6):

| Neck | C1 to C8 |
|---|---|
| Back | C1 to S3 |
| Diaphragm (central) | C3 to C5 |
| Upper Extremities | C5 to T1 |
| Thoracic Wall | T1 to T11 |
| Diaphragm (peripheral) | T6 to T11 |
| Abdominal Wall | T6 to L1 |
| Lower Extremities | L2 to S2 |
| Perineum | L4 to S4 |

The autonomic nervous system regulates the glandular and smooth muscular activity of the body. The system is divided into two parts: the sympathetic and the parasympathetic. Broadly speaking, each system antagonizes the effect of the other. The central connection of the autonomic system is integrated within the nervous system and with the central connection of the somatic sensory and the voluntary motor connection. Peripheral connection between the brain stem or spinal cord and the affected tissue are intermingled with the other components of the peripheral nervous system. The peripheral connection of the autonomic system consists of the efferent motor fiber and to a less extent the afferent fibers. The afferent fibers are mainly certain visceral sensory nerves that accompany the motor efferent nerves.

Many of the principles by which physiologic monitoring apparatus operates have counterparts in man's own instrumentation system. Through these systems, man is able to detect not only the five senses, but also many other types of sensation without mechanical or electronic aid. Impulses may be received from a source remote from the body (by telereceptors), from a source in physical contact with the body (by exoreceptors), from a source adjacent to and subsequently taken into the body (taste or smell) (by interoreceptors), or from within the body itself (by proprioreceptors).

The impulse is received and converted to an electric current (neural impulse) by an end organ specific for that type of stimulus. After being converted, the signal is transmitted to the central nervous system, where the impulses from a number of similar endings are stored, correlated, intensified, or suppressed, and sent on to higher relay stations further cephalad in the central nervous system. Ultimately, the impulses reach the center of the conscious perception and cerebral cortex where they are acted upon—either stored in memory cells, or made to initiate some motor response—or both.

This chain of events pick-up, conversion, correlation, and activity is similar throughout the various components of the detection system of the human nervous system, and resembles markedly some instrumentation made by man that are designed to detect, record, and control through servo mechanisms the physical and physiological responses in the experimental animal or patient.

The end organ is often referred to as a transducer. It essentially converts energy from one physical form into another. Impulses from the touch and pressure receptor in the skin reach the dorsal spinal nerve root ganglia via an axon of an afferent neuron. Dendrites of these neurons enter the zone of lissauer and engage in multisynaptic relay with other nuerons in the substantiagelatinosa. Correlation of impulses with intensification of the impulse probably take place in this area.

Correlation of tactile and pressure exterioreceptor impulses with a source coming from the proprioreceptors takes place in the venterolateral nucleus of the thalamus. Thalamocortical pathways conduct this stimulation to the area in the cerebral cortex wherein the sensation is experienced. It appears that some perception takes place at the thalamic level, at least perception of painful stimuli. The perception of other sensory modalities, as well as localization of all such modalities including pain, however, takes place in the cerebral cortex.

Testing of the somatic sensation, motor and sympathetic function of the body is done for a variety of medical and surgical reasons such as neurological examinations and evaluation. Essentially these methods of testing are to detect interruption of the pathway of output and/or input of the human nervous system.

An example of pathways interruption could be within the central nervous system that includes the brain and the spinal cord, or along any part of the pathway between the central nervous system and the peripheral one, including the peripheral receptors, or effectors. Conditions such as burns could affect the peripheral receptors while the central nervous system could be affected by disease, injury or general anesthesia. In general, some of these interruptions of pathways could be permanent or temporary that could present with variable degrees affecting one or more of the dermatomal, sympathotomal, sclerotomal, and myotomal regions.

An example of a permanent block used for therapeutic purposes is the neurolytic nerve block. The primary aim of a neurolytic nerve block is the permanent destruction of nerves that carry pain sensation. These are of great value in the management of certain types of chronic pain syndromes, such as cancer pain. Percutaneous, surgical cordotomies and rhizotomies are other examples of permanent blocks.

Examples of a temporary type of interruption (reversible block) that are commonly now used in clinical practice include spinal, caudal and epidural anesthesia. In these nerve blocks, the injection of local anesthetic drugs into the spinal canal or the epidural space results in a variable degree of somatic and non-somatic sensory interruption, sympathetic block and motor block. The depth and level of the anesthetic depends on various physiological and pharmacological factors related to the distribution of the anesthetic drugs, etc.

Testing of the somatic sensation is simply performed in order to test the integrity of the various somatic sensations in a particular region. There could be decreased form of sensation (hypoesthesia) or complete loss of sensation (anesthesia). In addition, in certain conditions, there could be an increased form of sensation or higher sensitivity (hyperesthesia). Complete loss of pain sensation is termed analgesia and an increase in pain sensation is termed hyperalgesia, while a moderate loss of pain sensation is termed hypalgesia.

Various noxious impulses can arise from the skin surface, deep issue and internal structure such as the viscera as follows:

1. Superficial perception of pain (cutaneous). Afferent impulses in response to a large number of different stimuli such as heat, cold, pressure and chemical release by injury or ischemia are received in an intricate network of fine nerve endings while they spread over the skin surface. These peripheral receptors behave differently under varying circumstances. For example, touch is perceived when the nerve endings are gently deformed, but when the same structures are vigorously disturbed by the violent contact of traumatic injury resulting in pain, and a similar sensation is perceived when the receptors are stimulated by a metabolite of tissue damage. The current view is that the pattern of response created by stimuli of varying intensity is more important than any particular quality of initiating stimulus. It seems that the skin has different thresholds for a variety of noxious impulses which create their own distinctive imprint in time and space in much the same way as a dot on a television screen develops into a recognizable picture. In general, pain emerging from the skin is described as burning in contrast to dull ache often experienced after injury to the deep tissue. This form of pain that arises from the skin is biphasic in nature and is well illustrated by the response to a sharp needle prick. Initially, following the needle prick there is almost immediate recognition of the first wave of rapidly transmitted impulses which is followed by a second, or delayed wave of sensation. This is the result of the next volley of slower conducted impulses that are transmitted to the spinal cord and has its own distinctive quality sometimes referred to as "stinging". It is important to recognize that the cutaneous sensation of pain has a dual double pattern;

2. Deep perception of somatic pain. In marked contrast to the precise information of pain from the skin surface (which is marked out as a clearcut zone known as the dermatome), the region of deep tissue served by a single posterior nerve route (or by a different autonomic nerve) is called the scleratome. However, this, unlike a dermatome, is not easy to define. Deep pain is usually experienced as a dull ache which is difficult to locate precisely. This in turn, is mediated by a wider large number of posterior nerve roots. Deep somatic structures vary greatly in their insensitivity to pain, and this is dependent on the distribution of nerve endings. Periosteum, deep fascia, ligament and capsule are joined in sheaths of nerve and blood vessels and are known to be highly responsive, while muscles are less sensitive and also articular cartilage and compact bone. Undifferentiated networks of nervous tissue are similar, but much less numerous than they are in the skin, are found in this deeper structure. Clinically, it is recognized that noxious stimulation from tendon, ligament and periosteum are often accurately reported, while those arising from the muscles are often ill-defined and sometimes confused with those from other deep structures;

3. Deep non-somatic perception of pain (visceral pain). This form of pain is mediated by the autonomic nervous system. The pain has definite characteristics that differ from the superficial pain, but in certain ways are similar to that evoked from other deep structures. The pain is usually poorly localized, dull and burning and is accompanied by several manifestations of autonomic activities such as pallor, bradycardia and hypotension and other cardiovascular changes. The intensity of deep, non-somatic pain is often high, although there are relatively few receptors in a hollow organ, such as the bowel. The noxious impulses are aroused by sudden distention or irritation and contraction of smooth muscle, possibly resulting from mechanical stimulation during surgery, toxic substances that are released during the process of injury, or inflammation; and 4. Referred pain. In certain conditions, noxious stimulations that arise from deep structures and internal organs could cause pain in overlying dermatomal regions of the skin or in a remote cutaneous region. Referred pain that arises from somatic structures such as muscle or bone is often misinterpreted as coming from other deep tissue, but never from a certain dermatomal region.

DESCRIPTION OF INVENTION

Referring to the drawings, FIG. 1 shows a block diagram of a sensory monitoring system 11 useful in practicing the system and method of this invention.

As shown in FIG. 1, system 11 provides a scanning apparatus capable of continuous monitoring of depths and levels of sensory and sympathetic blocks. The system may be entirely automatic or a portion may be performed by an operator. In addition, as indicated in FIG. 19, monitoring system 11 can be a part of an overall automatic anesthetic delivery system.

As shown in FIG. 1, a selective element stimulator 13 provides selective stimulation to the elements (typically electrodes) of a multiple element transmitting unit 15, which unit is non-invasively positioned contiguous to the skin of a patient 17. Stimulator 13 can be manually activated by a manual activator 19 or can be automatically sequenced by means of an adjustable timer 21, the energization of which is controlled by off/on switch 23.

A physiological response detector 25 receives the sensed output from the elements (typically electrodes) of a multiple element sensing unit 27, which unit is also non-invasively positioned contiguous to the skin of a patient 17. Physiological response detector 25 provides an output to comparator 29, which comparator also receives, as a second input, a reference level input from reference unit 31. The output from comparator 29 provides a stop signal which is coupled to selective element stimulator 13 to terminate stimulation when a predetermined reference level is exceeded.

A display unit 33 is provided to display information. First and second displays 35 and 37 are connected with selective element stimulator 13 for display of the sensed stimulation intensity level and the particular site then selected, respectively. In addition, the stop indication signal from comparator 29 is also coupled to display unit 33 and, more particularly is coupled to stop indication display 39, while an output from physiological response detector 25 is coupled to evoked response display 41.

Selective element stimulator 13 is shown in more detail in FIG. 2. As shown, the output from timer 21 and manual activator 19 are coupled through OR gate 45 to stimulator control unit 47, which control unit also receives the stop signal from comparator 29. Stimulator control unit 47 provides the level control and also the activate command signal to pulse stimulator 49. The output from pulse stimulator 49 is coupled to display unit 33 (and, more particularly, to stimulation intensity display 35 of unit 33) and to selector unit 51. A second input to selector unit 51 is provided from selector control unit 53 which receives an output from stimulator control 47. An output from selector control unit 53 is also coupled to display unit 33 (and, more particularly, to the site selected display 37 of unit 33). The output from selector 51 is coupled to the multiple element transmitting unit 15.

Multiple element transmitting unit 15 is preferably an array of energy transmitting components, transducing elements, or energy transmitting pathways. These elements deliver the stimulation energy to one or more of a particular dermatomal site or sites. Typically, the elements of multiple element transmitting unit 15 may be electrodes with connecting wires for electrical stimulation. Such elements could also, however, be an array of heating elements, fiber optic bundles, acoustic or ultrasonic elements, an array of electrical to mechanical activators, or an array of channels for the passage of gas or fluid.

The conducting electrodes provide for sequential monitoring of sensory, sypathetic, and motor block levels and depths. The electrodes are non-invasively applied to the skin for the purpose of either transmitting energy (or stimulation), or receiving physiological information. Electrodes are chosen with a view toward: avoiding damage or injury to the skin or internal body organs; enhancing safe operation (for example, the strength of stimulation delivered is not allowed to exceed an upper safe limit set by the apparatus and implimented by a stop command to prevent excessive stimulation); avoiding discomfort and allergic reactions; insuring adequate fixation to the skin surface (a given dematomal area) in order to insure accurate transmission of energy of stimulation and/or receiving physiological information required; reliability for continuing use over a relatively long period of time (without being adversely affected by washing, scrubbing solutions during the process of surgery, or by water, saline, blood or localized sweating at the attachment site of the skin), and sterile (preferably the electrodes are supplied in a sterile package for use during surgical procedures).

Figure 5A:
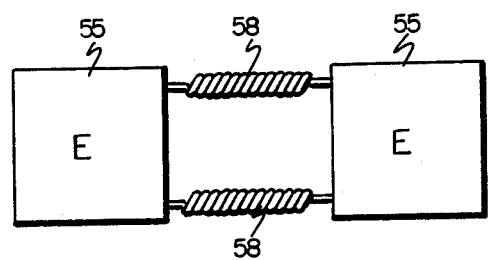
FIGS. 5A and 5B are front view sketches of the stretchable electrode with FIG. 5A depicting the electrode in an unstretched condition and FIG. 5B depicting the electrode in a stretched condition.
Figure 5B:
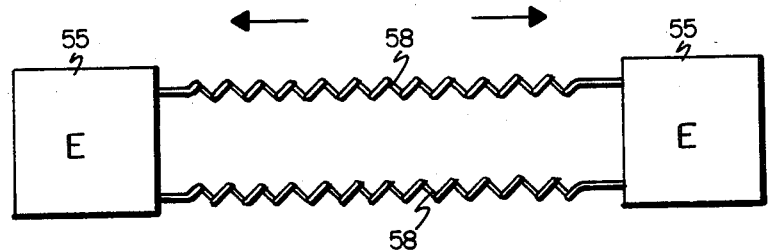

When utilizing electrical energy, a plurality of electrodes 55 are normally utilized. Such electrodes may include, for example, an electrode array positioned on a strip of insulating material 56, such as shown in FIG. 3, and are preferably utilized with the electrodes being non-invasively positioned on the body of a patient as illustrated, by way of example, in FIG. 4. The electrode array has a plurality of wires 57 extending from the electrodes 55 of the array for connection in monitoring system 11 as the multiple element transmitting unit 15 and multiple element sensing unit 27. An example of electrodes 55 connected between wires 58 to allow positioning of the electrodes at varying distances is shown in FIG. 5 (if the electrodes are connected in parallel then the wires 58 may also be utilized to carry current to and from the multiple sensing unit 27. Other examples of electrode systems that might be utilized for use with other forms of energy are an electrode array with connecting heating element, fiber optic bundles, acoustic or ultrasonic elements, an array of mechanical activators, and an array of channels for the passage of gas or fluid.

The elements of multiple element sensing unit 27 must be elements that transmit information from the skin of a patient to the apparatus. This information consists of evoked and non-evoked physiological changes transmitted from the skin surface. Electrode arrays non-invasively positioned on the body of a patient are illustrated in FIGS. 7, 10, 11, 12, 13, 14 and 15. As shown, the electrodes 55 may be coupled to the monitoring system 11 through a junction 59 (which may be utilized to provide selective element stimulation) and connectors 60 (for connecting each electrode to junction 59 through leads at each side of each connector as shown).

Figure 7:
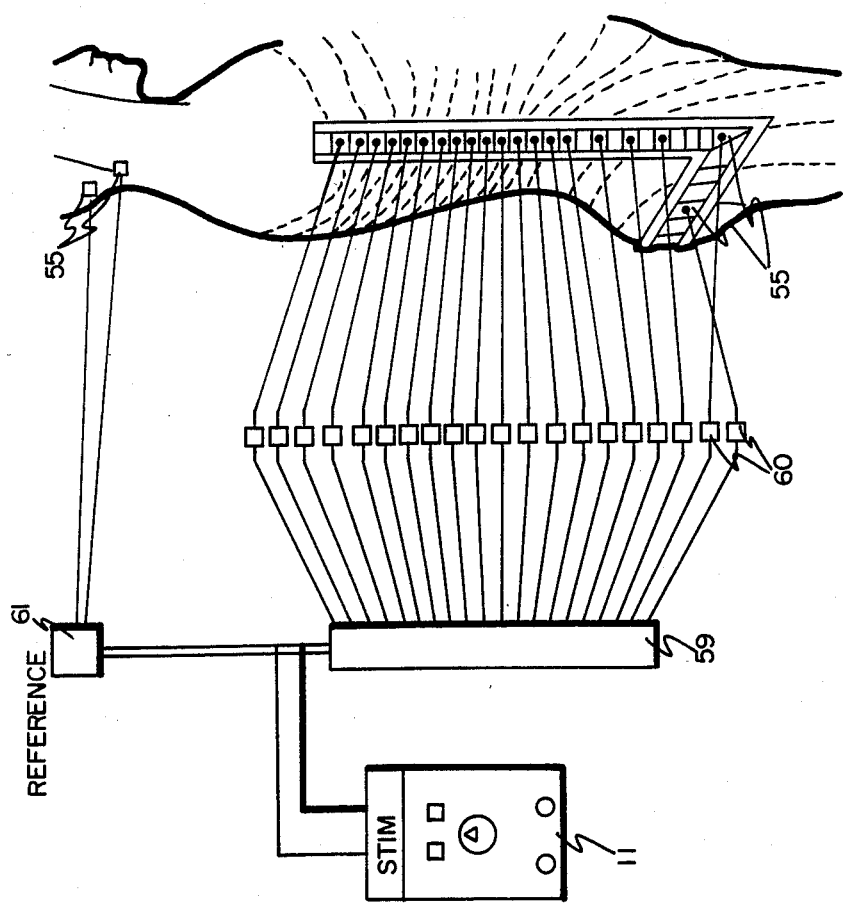
FIG. 7 is an illustrative sketch of an electrode arrangement on a patient in conjunction with a monitoring system.

As shown in FIG. 7, for example, a reference signal may be provided from electrodes 55 and coupled through reference signal detector 61 to monitoring system 11 and junction 59.

Figure 8:
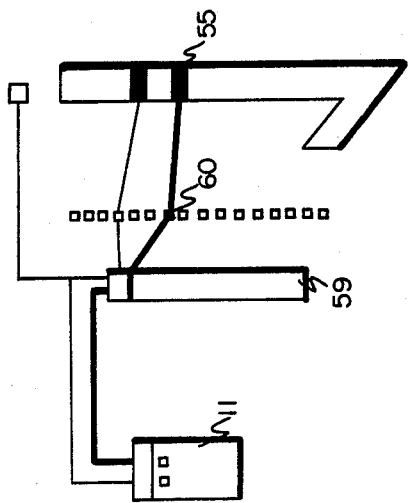
FIGS. 8 and 9 are illustrative sketches illustrating stimulation of one and a plurality of electrodes, respectively.
Figure 9:
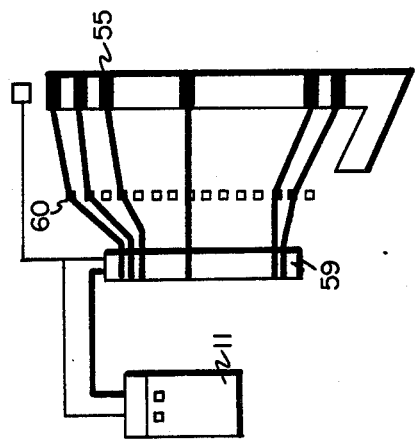

As shown in FIG. 8, one specific electrode may be stimulated from monitoring system 11 through junction 59 and connectors 60, or, as shown in FIG. 9, a plurality of electrodes may be simultaneously stimulated from monitoring system 11 through junction 59 and connectors 60.

Figure 10:
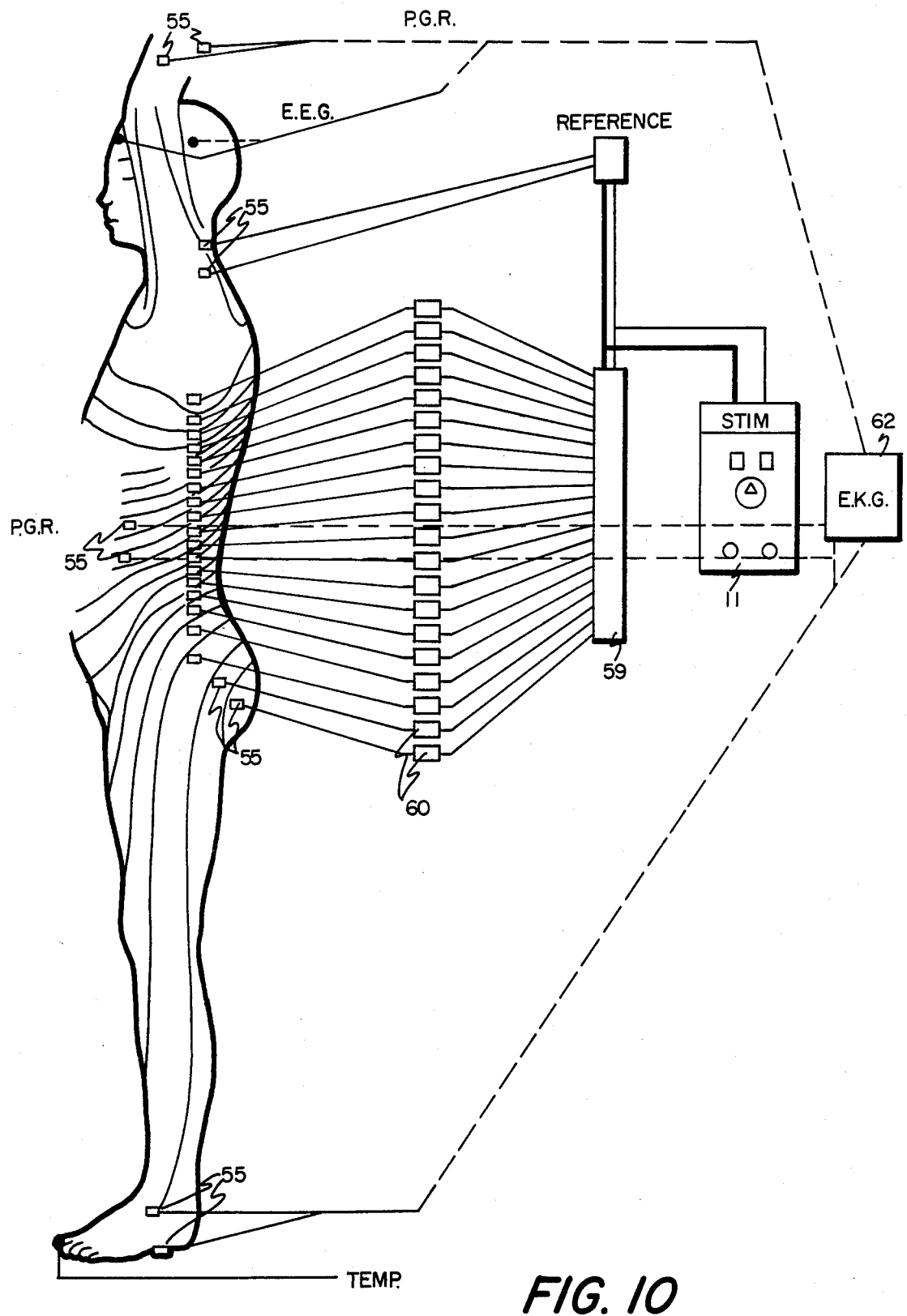
FIG. 10 is an illustrative sketch of an electrode arrangement on a patient in conjunction with a monitoring system and and EKG system.

A number of various other types of electrode systems (at least some of which are already on the market) might also be utilized for transmitting such information with such systems including EEG, PGR, EMG, EEMG, skin temperature, and ultrasonic devices for measuring regional skin blood flow. As shown in FIG. 10, by way of example, an Electrocardiogram (EKG) unit 62 may be utilized in conjunction with monitoring unit 11 and electrodes 55.

For most effective use of electrode arrays, the elements of multiple element transmitting unit 15 and multiple element sensing unit 27 are positioned adjacent to one another, as well as being positioned adjacent to the skin of the patient (the elements may overlap one another as needed).

The selection of attachment sites that can be used for transmitting energy of stimulation and/or for receiving physiologic information is as follows (by way of example):

1. With the reference site along the $C_{3-4}$ dermatomal site (as shown in FIG. 6), the electrodes of the elements are preferably placed bilaterally for monitoring the sensory and sympathetic block level so that one acts as a stimulation control and the other acts to monitor the sympathetic changes such as PGR. Alternately, the reference site could be along the trigeminal nerve distribution or facial nerve distribution in the face, acting as a control for monitoring the sensory, sympathetic, and motor block levels and depth. In addition, EEG electrodes (if used) could be incorporated into the electrode system; or 2. With the dermatomial site to be tested as one or more dermatomial sites (also sympathatomal and myotomal), the position of the site or sites is choosen either unilaterally or bilaterally along the back, side or front of the human trunk and/or circumferentially (circularly) across the trunk and/or the upper or lower limb. A multipurpose electrode system is defined herein as a system in which stimulation is conducted to the entire dermatomal, sclerotomal, myotomal and sympathatomal regions of the body, and at the same time conducting and transmitting information such EEG, PGR, EMG, ultrasonic changes, or temperature, and a response to stimulation or no stimulation at both the reference and the tested dermatomal sites.

The types and shapes of the electrodes and their dimensions are dictated by the use contemplated. The dimension of an individual electrode or group of electrodes depends on the site of the position of the dermatome (along the back, side or front of the human trunk), the age and size of the patient. A stretchable type of electrode can be used in the different sites. The number of electrodes depends upon the required needs of monitoring. For the majority of surgical procedures, for example, that involve the perineal region, lower limbs, lower abdomen, and upper abdomen, a system can be used whereby a single electrode supplies each of the dermatomal sites in groups as follows:

| | |
|---|---|
| Sacral | S 5, 4, 3 |
| | S 2, 1 |
| Lumbar | L 4, 5 |
| | L 1, T 2 |
| Thoracic | T 11, T 10 |
| | T 9, T 8 |
| | T 7, T 6 |
| | T 4, T 5 |
| | T 3, T 2 |
| | T 1, C 7 |
| Reference Sites | C 3, 4 × 2. |

Figure 13:
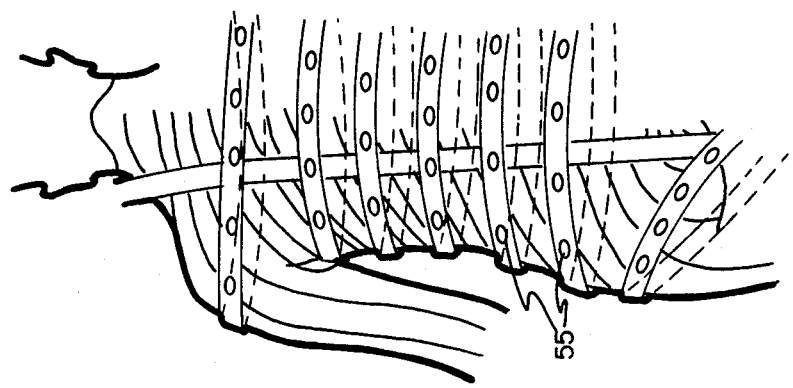
FIGS. 11, 12 and 13 are illustrative sketches of positioning arrangements of electrodes.
Figure 12:
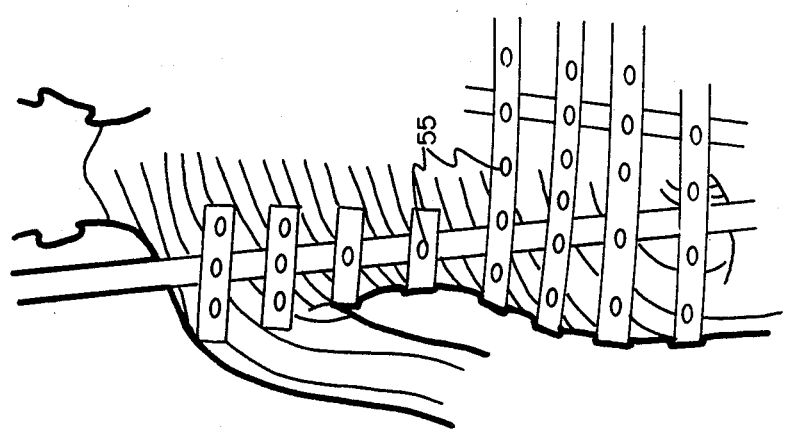
Figure 11:
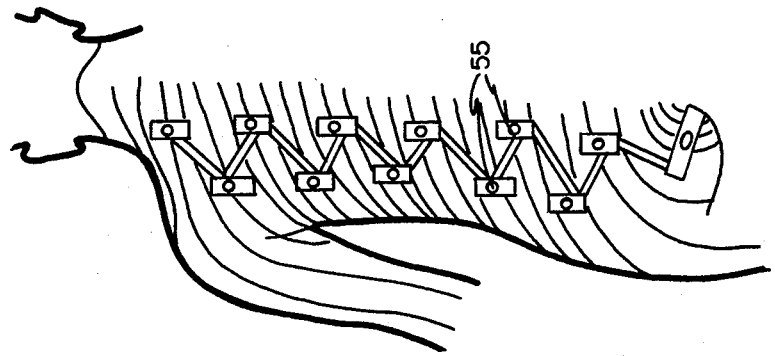

Illustrative positioning of electrodes (in addition to those shown in FIGS. 7 and 10) are shown in FIGS. 11, 12 and 13, with FIG. 11 illustrating a zig-zag pattern of electrodes 55, FIG. 12 illustrating a unilateral/bilateral arrangement of electrodes 55, and FIG. 13 illustrating a circumferential arrangement of electrodes 55.

When electrical stimulation is used, the electrode system is made of conductive and/or non-conducting rubber, and/or a conducting alloy and/or copper separated by non-conducting material such as nylon or foam. The structure is preferably flat for skin fixation over a prepared dimension (as described above), and is configured so as to not interfere with surgical procedures. Adhesive material is preferably provided to insure adequate fixation to the skin.

The electrodes can be made of disposable material that is easy to use which can include removing an adhesive paper exposing series of interrupted copper electrodes covered with an appropriate amount of conducting jelly, ready for use. Adhesive material is present around and between the copper electrodes to insure adequate fixation to the skin. The covering of the electrode on both sides may be made of sponge for patient comfort.

This type of electrode system is for delivering electrical stimulation and also for transmitting physiological information such as PGR. Alternately, the electrode system can be made of reusable material. For example, the electrode system could be made of conducting rubber in different sizes and shapes as illustrated with the electrode being fixed to the skin using an adhesive tape following the application of an appropriate amount of conducting jelly.

As brought out hereinabove, the delivery of the stimulating energy to the dermatomal sites is accomplished through the use of a selective element stimulator 13. While selective element stimulator 13 is shown in FIG.

2 to include a pulse stimulator 49 controlled by a stimulator control 47 and a selector 51 controlled selector control 53, it is to be realized that other arrangements could be utilized. Other arrangements could, for example, include the use of a set of controllable stimulators instead of a single one with each stimulator being controlled for sequential activation.

Figure 14:
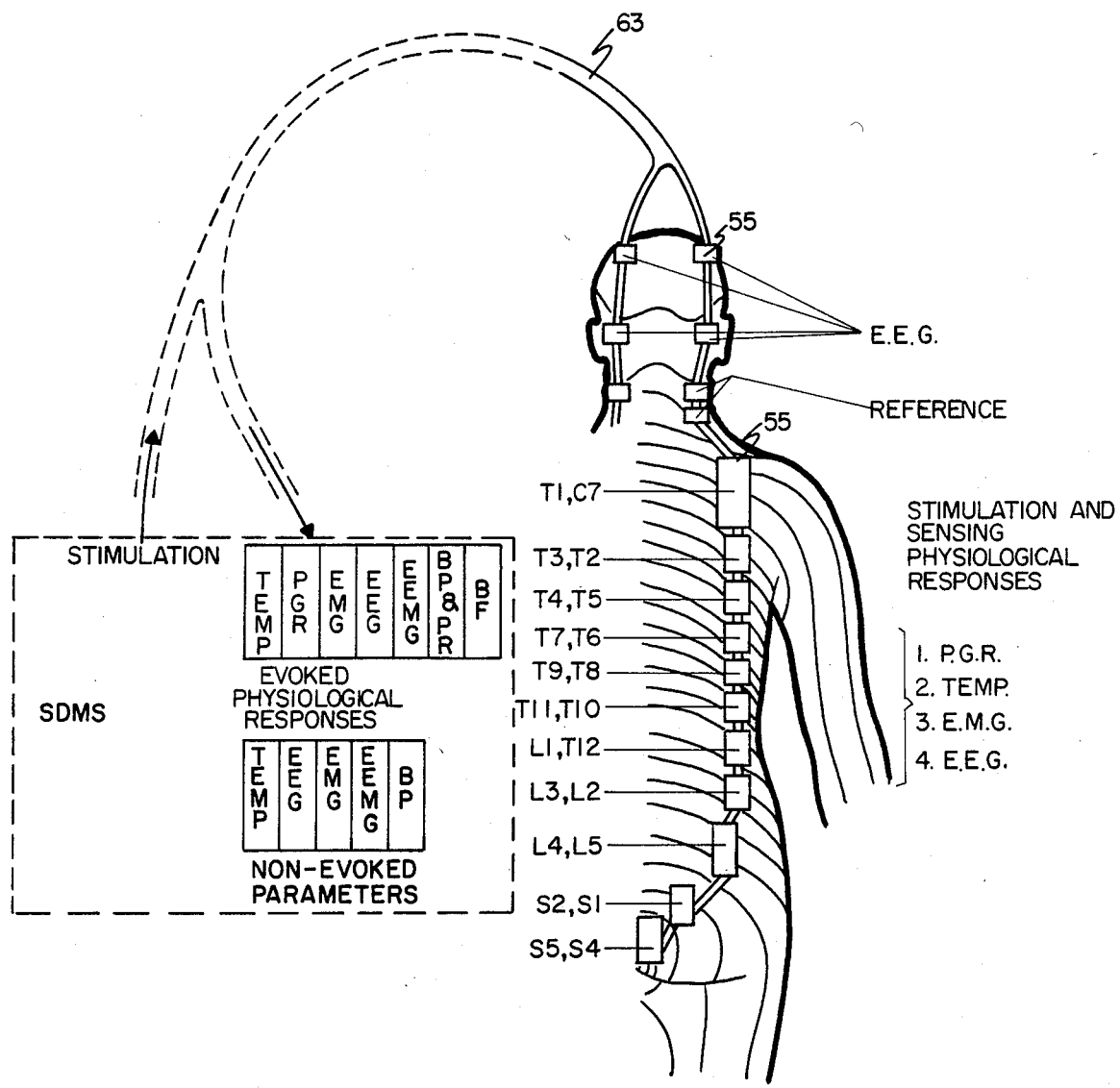
FIGS. 14 and 15 are illustrative sketches of a multipurpose electrode system positioned on a patient.
Figure 15:
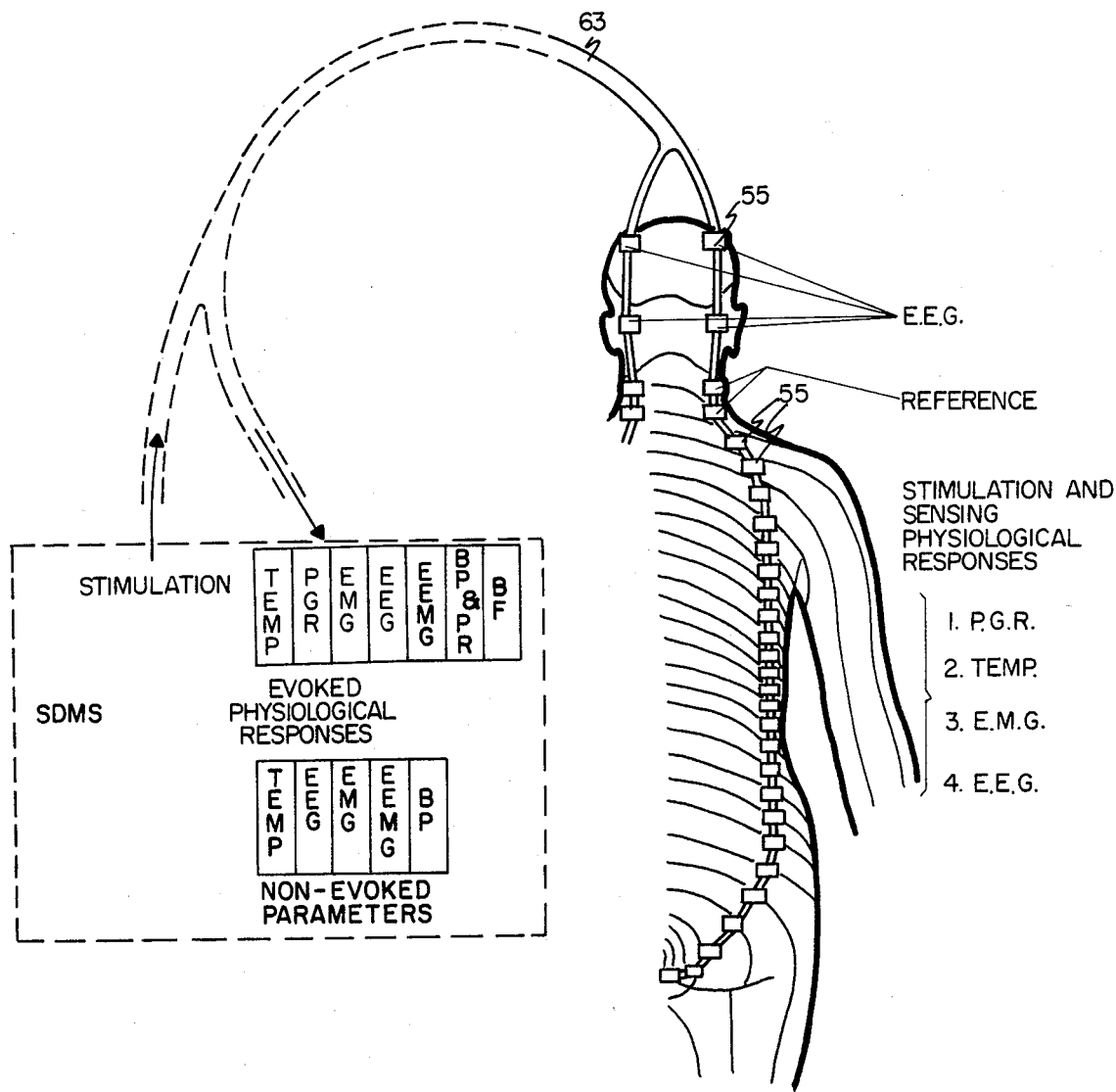

As indicated in FIGS. 14 and 15, the electrodes 55 may be connected with individual wires of a single continuous cable 63 to form a multipurpose electrode system for measuring a plurality of physiological evoked responses or physiological non-evoked parameters. Examples of physiological non-evoked parameters are: 1. Temperature (TEMP); 2. Electroencephalogram (EEG); 3. Electromyogram (EMG); 4. Electroencephalomyogram (EEMG); and 5. Regional Cutaneous Blood Flow (BF). Examples of evoked responses are: 1. TEMP; 2. PGR; 3. EMG; 4. EEG; 5. EEMG; 6. Blood Pressure and Pulse Rate (BP & PR); and 7. BF.

In any case, the purpose of the energy delivery from the stimulator 13 through the multiple element transmitting unit 15 is to deliver energy to stimulate the underlying structure (dermatome and sclerotomes) in order to test the nervous system perception of sensation, superficial and deep pain at various dermatomal and sclerotomal sites. This includes the site or sites to be tested and one or more reference sites for comparison. The source of the energy is kept under control so that the level can be made variable in strength to produce no sensation, very mild sensation, an unpleasant sensation to mild pain sensation, and/or a moderate to severe pain sensation (deep pain sensation).

A second purpose of the energy delivery is to stimulate the dermatone in order to test the sympathetic integreity. This is done by stimulating the reference site (for example high up on the neck region) and recording the changes in cycle galvanic skin response (PGR) at the various dermatal sites and in sequential manner. Included in such an array can be a plurality of sensors or electrodes for detecting the patient's response to such stimulation, for example, using the electrodes for sensing the galvanic skin response.

For selection of the element to be activated, the selector can be, for example, an electric switch activated by manual means, relays, solid state, fluidic or air switches remotely or manually activated, or any other device that allows directing the energy from a single source input to one of many selectable outputs sites or stimulating devices.

As brought out hereinabove, the particular site selected for stimulation is preferably displayed at display unit 33 and may be recorded if desired. A display related to the magnitude of the applied stimulating energy (i.e., stimulation intensity display 35) is preferable to provide the user with an assessment of the level of energy that is then being transmitted at a particular dermotomal site or sites. Such a display can consist of indications on a switch or adjacent control in the simplest form or, preferably, may be a meter, a liquid crystal display or some other such display device. Such a display device might also contain a memory for storing and displaying the magnitude of applied energy from the time at which a stop scan command is produced by comparator 29 until the time at which the next start of a new scanning sequence is initiated.

Pulse stimulator 49 produces a pulse of energy each time it is activated by an activate signal from stimulator control 47. The level of the energy is controllable and is preset to a certain strength and then adjusted by either manual or automatic means by the stimulator control 47. Stimulator 49 can be an electric stimulator or any other energy generation device such as a device for generating laser energy and the like. The control circuitry for the level and activation could be combined in conjunction with other portions of the system as described.

The selector activator or control 53 could be a shaft of a switch where selector 51 is a rotary switch, for example, or may be more complex and consist of a counter and driver circuitry to activate relays, valves or solid state switches with the necessary logic and memory included. The command from advanced stimulation to the next site could be made in a complex manner to allow the stimulator to control itself to select the next site through pulse stimulator 49.

The site selected display 37 might be a simple visual display or could include a memory with the ability to display the last site that was stimulated and could, in its simplest form, be a particular switch or the location of a switch or switches, but is, preferably, a liquid crystal display, or a solid state light emitting diode, gas discharge, light projection or other such type of indicator. If the system is acting as an automatic scanning system, then the display would hold in a memory, when utilized, an indication of the site in which the stop command has been produced by comparator 29.

Stimulator control 47 consists of logic and control circuitry or a mechanism to set, or vary, the level of stimulation energy, initiate activation, and initiate the advance of the next dermatoma site. The control receives input information signaling it to begin its scan, or measurement sequence, which input can originate either from timer 21 or by manual activation of manual activator 19 (which can be activated by a patient). The stimulation is automatically stopped either by a stop indication output from comparator 49 or by an input from the manual activation actuator 19.

Automatic operation is carried out by adjustable timer 21 which provides a timing mechanism used to initiate and control each scanning cycle in a sequential manner. One cycle of a scanning sequence is defined as the total scanning process that determines the level of the sensory and sympathetic block at a particular point in time and a response to a certain strength of stimulus and under certain patient conditions. A new cycle is initiated after a time period has elapsed to determine if the level of the block has changed. The time period between cycles may range from one to thirty minutes and the timer, therefore, is set up to the desired time period. The timer could be shut off and/or each cycle initiated manually. The system is not dependent on the timer alone since manual activation can be utilized, as indicated in FIG. 1.

Comparator 29 receives the invoked response due to the applied stimulus at the various dermatomal sites to be tested and compares this response against that obtained from a reference level or criteria (i.e., the response from an element placed in the neck region, for example). Application of the reference level need not be performed at every cycle of comparison as the evoked response can be compared to the previous response from the reference level unless otherwise indicated (i.e., held in a memory circuit).

The strength of the stimuli that is applied to the reference level and subsequent measurement should not exceed that which produces a strong sensation to the mild pain sensation and/or should be gradually increased in strength until the evoked response is obtained in order to assure the patient's comfort. The strength of stimulus, as applied to the testing site should be equal to that applied to the reference level, 1½, 2, 2½, and 3 times as much. If a change occurs in the evoked response that is greater than the preset reference level, a stop command is issued and coupled from the comparator to selective element stimulator 13.

In practice, a stimulator was utilized having ten (10) different settings. Table I illustrates the settings with respect to values as follows:

TABLE I

| Setting R | Stimulation Frequency Hz | Setting PW | Pulse Width (micro sec) |
|---|---|---|---|
| 1 | 14.3 | 1 | 45 |
| 2 | 15.4 | 2 | 80 |
| 3 | 17.2 | 3 | 100 |
| 4 | 20 | 4 | 130 |
| 5 | 25 | 5 | 150 |
| 6 | 26.3 | 6 | 180 |
| 7 | 33.3 | 7 | 200 |
| 8 | 40 | 8 | 220 |
| 9 | 55.5 | 9 | 240 |
| 10 | 100 | 10 | 270 |

Table II illustrates measured values output voltage (E) and current (I) with respect to particular settings and stimulator load resistance (R) as follows:

TABLE II

| R(K) | DIAL = 10 | | DIAL = 8 | | DIAL = 6 | | DIAL = 4 | | DIAL = 3 | |
|---|---|---|---|---|---|---|---|---|---|---|
|  | E (v.) | I (ma) | E (v.) | I (ma) | E | I | E | I | E | I |
| 15 | 100 | 6.7 | 104 | 6.9 | 94 | 6.3 | 96 | 6.4 | 27.5 | 1.8 |
| 10 | 96 | 9.6 | 98 | 9.8 | 96 | 9.6 | 96 | 9.6 | 22.5 | 2.3 |
| 8 | 94 | 11.8 | 96 | 12.0 | 94 | 11.8 | 94 | 11.8 | 20.0 | 2.5 |
| 6 | 92 | 15.3 | 94 | 15.7 | 90 | 15.0 | 88 | 14.7 | 17.0 | 2.8 |
| 4 | 88 | 22.0 | 88 | 22.0 | 86 | 21.5 | 60 | 15.0 | 12.5 | 3.1 |
| 2 | 76 | 38 | 76 | 38.0 | 64 | 32.0 | 36 | 18.0 | 7.0 | 3.5 |
| 1 | 56 | 56 | 54 | 54.0 | 37 | 37.0 | 19 | 19.0 | 3.8 | 3.8 |
| .8 | 49 | 61.3 | 44 | 55.0 | 30 | 37.5 | 16 | 20.0 | 3.0 | 3.8 |
| .6 | 38 | 63.3 | 34 | 56.7 | 22.5 | 37.5 | 12 | 20.0 | 2.3 | 3.8 |
| .4 | 26.5 | 66.3 | 22.5 | 56.3 | 15.0 | 37.5 | 8 | 20.0 | 1.6 | 3.9 |
| .2 | 13.5 | 67.5 | 11.4 | 57.0 | 7.6 | 38.0 | 4 | 20.0 | 0 |  |
| .1 | 7.0 | 70.0 | 5.6 | 56.0 | 4.0 | 40.0 | 2 | 20.0 | 0 |  |

The operator or patient may provide the comparison. The evoked response is compared against a sensation, an unpleasant sensation to mild pain sensation, and moderate to severe pain sensation (or alternately, a scale of 0 to 10 for sensation and pain sensation, where 0 is no pain and no sensation is felt and 10 is severe pain that the patient can not tolerate). The evoked response is then compared by asking the patient to determine when the sensation exceeds a certain point. The patient may signal a particular sensation or this signaling may be in the form of the pressing of a control, such as a switch, in a particular fashion.

The evoked response that is detected by the physiological response detector results from the application or no application of a stimulus by the monitoring system to be used for monitoring the sensory system, the sympathetic system, and also the motor system. In monitoring the sensory system, the simplest case (when the patient is awake) may consist of a switch that the patient depresses (or alternately the operator depresses when hearing or observing a significant response from the patient). In a more complicated version of the system, the electromyogram, skin galvanic response, evoked electroencephalogram, physiological changes in pressure or pulse rate or other physiological measurements may be used in detecting a response to the applied stimulous. The attachment sensor may consist of part of an array of electrodes for applying stimulation and/or the attachment sensor transmits psychological changes or parameters without stimulation such as regional skin temperature, regional skin blood flow by ultrasonic means, muscle electric activity (EMG), or other physiological change. The output from the patient is either objective or subjective. The objective output could be in the form of evoked responses or non-evoked physiological parameters. For the purpose of comparison, a control (reference site is used) and this is selected in an area higher up in the neck region or face. For monitoring sensation (dermatomal and scleratomal) the application of stimulus is required, while monitoring the sympathetic and motor block level could be done with or without the application of stimulation at tested and control sites.

Figure 16:
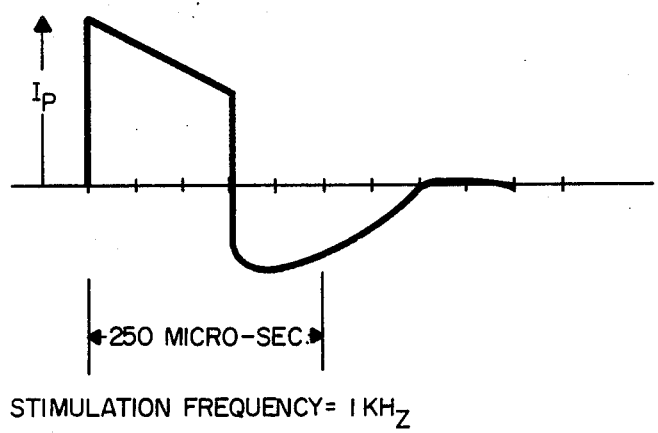
FIGS. 16 and 17 are waveforms illustrating typical stimulation outputs.
Figure 17:
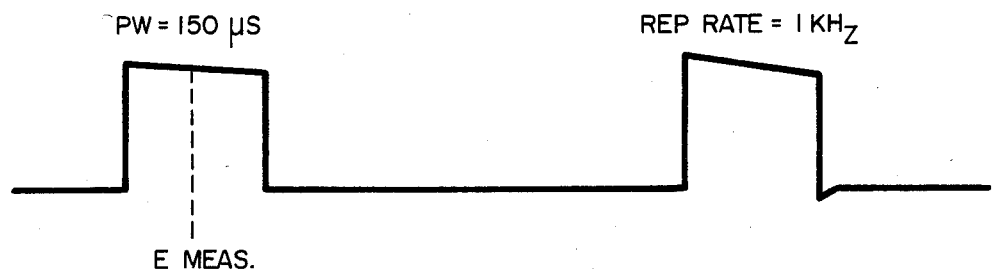
Figure 18:
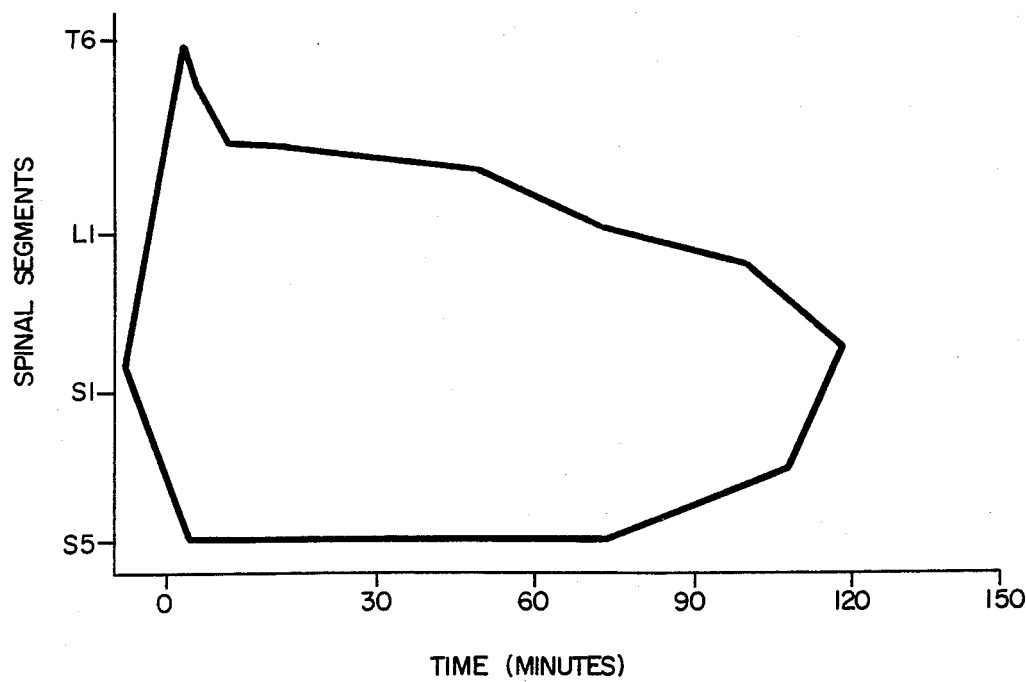
FIG. 18 is a graph illustrating typical measured segmental changes in spinal anesthetic blocks.

A typical waveform with a stimulation frequency of 1 kHz is shown in FIG. 16, with FIG. 17 showing a typical pulse train at a 1 kHz stimulation repetition frequency. With an Ip of 2 ma., a tested patient reported a barely perceptive sensative; with an Ip of 4 ma., the patient reported a strong, but not painful, sensation; with an Ip of 5 ma., the patient reported the start of pain; with an Ip of 10 ma., the patient reported pain (tolerable); and at an Ip of 12 ma., the patient reported a very painful condition. FIG. 18 illustrates typical measured segmental changes in a spinal anesthetic block, as determined by application of specific stimulation with an Ip of 5 ma. using the apparatus, and in response to a single administration of anesthetic dose.

This invention has been found to be particularly useful for monitoring the adequacy of the administered anesthetic during surgery. This invention is also particularly useful for monitoring painful nerve interruptions to the sensory system of a patient undergoing surgery under a regional nerve block. In such case, the area upon which surgical procedures are being performed, as well as areas adjacent thereto, are monitored to ensure continuous patient safety and comfort. Information from these areas, along with reference information (normally obtained from remote areas of the patient) are utilized in such monitoring, and can be utilized to provide the clinician with means to more accurately assess the need for additional anesthetic and/or to enable the clinician to more accurately respond to a patient and/or surgical need.

The system and method of this invention were utilized in testing of patients, and compared to standard methods of testing sympathetic, sensory and motor blocks. Fourteen patients were studied. In four, spinal anesthesia was used, in nine others, a continuous epidural anesthesia was used, and one had a spinal cord injury.

The group of patients given spinal anesthesia were of average weight and height for their age, which ranged from 24 to 82 years. These patients were undergoing various orthopaedic surgery of the lower limbs and hip regions. The spinal anesthetic was performed in the usual manner using hyperbaric solution of tetracaine. The anesthetic dosages were adjusted to the patient's age and type of surgery. Preoperatively, the patients were examined neurologically and they were premedicated with appropriate dosages of euscos (a tranquilizer and neuroliptic drug). All patients received intramuscular ephedrine in a dose between 25–50 mg. that was injected immediately prior to the commencement of the block. In addition, they received a preload of 500–1000 ml. of Ringer's lactate. The patients were studied before commencement of the surgery, during surgery, and in the recovery period until the anesthetic wore off and complete return of normal sensation occurred.

The patients given epidural anesthesia were between the ages of 32 and 86 years and were within average weight and height for their age, with the exception of one patient who was extremely obese. This group of patients were undergoing various upper and lower abdominal surgery. All patients were examined and managed preoperatively in a similar way to that described above in the spinal group. Seven patients received continuous lumbar epidural anesthesia, where an epidural catheter was inserted in $L_{3,4}$ interspace. Two patients received continuous thoracic epidural, where an epidural catheter was inserted at $T_{7,8}$ interspace. Mepivacaine (carbocaine) in a concentration of 1–2% was used with the appropriate volume for the particular type of surgery. Again, all patients were studied before commencement of surgery, during surgery, and in the postoperative period. In the latter case and for the purpose of postoperative pain relief, the epidural catheter was left in situ in all patients for a period of 24–38 hours. A continuous pump infusion was attached to the epidural catheter via an epidural filter. Using the pumping system, a continuous infusion of a solution of 0.5% mepivacaine (carbocaine) was used at the flow rate of 1–2 drops per minute. The patients were kept in the intensive care unit and blood level of mepivacaine was estimated at frequent intervals. Moreover, the requirement to maintain a certain level of sensory anesthesia that is compatible with complete pain relief was examined and assessed continuously. On occasion, where the anesthetic was inadequate for pain relief, a bolus of 5–10 ml. of 1% mepivacaine was then injected. Or, alternatively, the infusion pump rate was increased. In the event where it was found that the anesthetic level was higher than that required for pain relief, or when cardiovascular changes or respiratory changes occurred as a result of higher level of sympathetic and motor block, infusion of the local anesthetic drug was terminated until return of normal function and reasonable anesthetic level.

A 14-year-old patient who was admitted to intensive care with a fractured dislocation of $C_1$ vertebra was studied. This patient remained on continuous ventilation for a period of approximately three months and was examined neurologically at frequent intervals.

The anesthetic level and depth were studied using the following methods:

1. Standard Common Methods of Testing a. Sympathetic: The progress of sympathetic block was assessed by the use of the alcohol cotton swab method applied at various dermatomal sites prior to the commencement of surgery and before and after the injection of a local anesthetic agent. During surgery it was performed in a way that does not interfere with the sterility of the procedures. In addition, the progress of sympathetic block was assessed by monitoring the skin temperature of the big toe and also the psychogalvanic skin response of the left foot before the injection of local anesthetic and throughout the study whenever it was permissable. The psychogalvanic response (PGR) was performed by stimulating the patient with a sudden sound or by the use of a pin prick to elicit pain;

b. Sensation: The Progress of the sensory block was assessed by measuring the time at which analgesia could be first detected at any dermatomal level using the pin prick method. Thereafter, the spread of block was measured every five minutes. The duration of sensory block was assessed until the time of complete return of all sensation; and c. Motor Power: The intensity of motor block was assessed every five to ten minutes or as permissable. This was performed by examining flexion and extension at the hip, knee, and ankle joint representing $L_2$-$S_2$ myotomes.

2. Sensory Dermatome Monitoring System (SDmS)

FIGS. 1 and 2 illustrate the monitoring system that was used. A unit of transcutaneous nerve stimulation was used as a source of variable electric stimuli. The stimulus was delivered at various dermatomal sites through the use of a number of connecting wires and attached electrodes which were positioned at various skin dermatomal sites. In addition, another set of electrodes was attached to the foot, chest wall, and neck for the purpose of recording the psychogalvanic skin response using a Seimens 4-channel recorder and oscilloscope. A third set of electrodes consisting of two bilateral electrodes and one reference in the middle were attached to the head for monitoring the electroencephalogram (EEG). The sensory monitoring system was used for monitoring sensation and sympathetic integrity.

Sensations were monitored either through subjective responses from the patient or through analysis of evoked response in the form of changes in PGR or EEG. In general, the selection of the various dermatomal sites for transmitting stimulation or receiving physiological responses was according to the requirement of surgery and was slightly varied in different patients. Two electrodes were attached at $C_{3,4}$ in the neck region. One for the purpose of transmitting the stimuation and the other for the purpose of recording changes in the PGR (control or reference site). The individual electrode and conducting wires were labeled according to their attachment site end whether they are transmitting or receiving information. The electrodes were positioned before commencement of the study using an appropriate conduction jelly and adhesive tape for fixation to the skin. The labeled wires that were attached to individual electrodes representing one or more dermatomal sites to be stimulated were connected directly to the unit of transcutaneous nerve stimulation one at a time, or, alternatively were connected to a metal bar in groups and the metal bar was then connected to a transcutaneous nerve stimulation unit (TCNS). This form of simple switching enabled the stimulus to be carried out to a single dermatomal site or multiple sites at the same time and as frequently as desired by the operator.

Testing of the sympathetic block was carried out through monitoring of the skin's galvanic response at the various dermatomal sites (foot, chest, hand, and neck) in response to electric stimulation of the unblocked dermatomal area at $C_{3,4}$ in the neck region.

The scanning process or cycle was performed as follows:

a. Subjective: All the patients were told that they would be tested with either the pin prick or with the use of a small electric current at a given time, and they were instructed to answer by saying A, B, C, D, or E (where A represented no sensation being felt, B represented just the feeling of commencement of sensation, C represented the commencement of a strong feeling of sensation, D represented uncomfortable sensation to mild pain, and E represented strong pain that the patient was unable to tolerate and wished the stimulus discontinued immediately. Following the full explanation to the patient, the scanning process was commenced by testing all of the electrodes individually at the various dermatomal sites including that of the reference site to insure that the system worked and to obtain a baseline. These baselines consisted of recording the strength of the stimuli as seen on the the dial of the TCNS unit which produced A, B, C, D, and E at each dermatomal site and in a sequential manner. This process was repeated three times and the mean value was then calculated. Following the injection of local anesthetic solution in a spinal or epidural space, the entire process was then repeated with the level of stimulation being gradually and progressively increased and was directed to the dermatomal area close to the site of injection that was likely to be blocked first, and also from time to time was directed to the reference site for comparison. The stimuli strength on the dial of the TCNS unit required to produce B, C, D, and E was continuously recorded. The process of cycling and switching the wires was continued every on to five minutes until either a change in the requirement of the stimulus producing B, C, D, and E, or until a maximum level on the dial of the stimulus was reached and which, in turn, produced no sensation. At this stage, stimulation of that particular dermatome or dermatomes was terminated and the whole process was repeated stimulating lower or higher levels of dermatomal site or sites. At these new site or sites, the stimulation again started at A level and progressively increased. The cycle was then repeated until all the required dermatomal sites had been tested to the maximal level of 10 (the required dermatome was selected according to the type of surgery and, for the purpose of safety, two consecutive dermatomes higher and lower were added to insure adequate block of all sensation that was about to be stimulated during surgery). The rest of the dermatomal sites were used to monitor further extension, in particular, higher extension of sensory and motor block beyond the desired one for surgery. These dermatomes, when appearing to have normal or reduced sensation, were not stimulated with the strength of stimulus that produced either E or the maximum level of 10 to insure patient comfort and safety;

b. Analysis of Evoked Responses: The psycholgalvanic skin response was monitored from $C_{3,4}$ in the neck region in response to electrical stimulation at various dermatomal sites using the levels that produced A, B, C, D, and E. In addition, sudden changes in the EEG that could be seen on the oscilloscope in response to stimulation were recorded (evoked EEG). Following stimulation of the various dermatomal sites that were to be tested, the PGR and EEG responses were compared to that obtained from the reference site $C_{3,4}$ using the same or different strength stimulation. The strength of stimulation that produced slight PGR response or slight evoked EEG response was then recorded. Excessive stimulation beyond that level of stimulation was not used during surgery. In all patients, the level of stimulation varied depending on whether or not the patient was given moderate to heavy sedation. In the latter case, subjective responses were not performed but instead, the evoked responses were used and analyzed. Following the sequential stimulation of dermatomal sites, and as the PGR started to appear in response to maximum stimulation or lower than maximum stimulation, this indicated persistence of sensation at a particular higher level of dermatomal site. Absence of PGR response due to stimulation (maximal) of all dermatomes that were chosen for a particular type of surgery and at the same time, insured that these particular dermatomes were adequately blocked and was particularly used in those patients who were given sedatives and narcotic analgesics. To insure that the response was not due to the sedation, a gradual and progressive stimulation was performed at the reference site ($C_{3,4}$) and a record of the strength of stimulus that produced the slight PGR was then noted and a comparison could then be made; and c. Sympathetic: The scanning process or sequence of monitoring the sympathetic block was performed by recording the psychogalvanic skin response in the foot, chest wall, upper arm and neck at $C_{3,4}$, and in response to stimulation of $C_{3,4}$ dermatomal area using B, C, D, or E. Excessive higher stimulation (E) was not used during surgery, unless heavy sedation was given and no response could be obtained using lower levels of stimulation. The control (reference site) was used first by stimulating the recording PGR responses at $C_{3,4}$. A slight response was considered sufficient. Then the same level of stimulation was used to test the foot responses, chest wall and upper arm in sequential manner. If no response was obtained, the level of stimulation was not increased. The sympathetic level in response to that particular strength of stimulation was then used. Following commencement of surgery, and at frequent intervals of 5 to 15 minutes, the process of scanning the dermatomal sites was then repeated. From previous data, it was often unnecessary to scan each dermatomal site, but instead, a group of dermatomal sites that were required for surgery (those that are stimulated by surgery, plus two dermatomes higher and lower) were stimulated to the same level at the same time. A low level of stimulation was used initially and the level was then increased until a response was obtained as maximum level was reached with no response being obtained. This was done to insure the continuity of the sensory blockade at the desirable site. In addition, scanning of the higher and lower dermatomal sites was performed individually as mentioned previously, the strength of stimulus did not exceed that which produced a mild sensation of pain. Alternatively, the use of evoked response in the form of slight alteration in PGR was considered sufficient to stop the stimulation process and not increase the stimulation strength to a higher level.

The Sensory Dermatomal Monitor System (SDMS) was clinically evaluated and compared with the standard methods of testing sensation and sympathetic blocks. From the results obtained during the onset and regression of spinal and epidural blocks, it was observed that while the skin appeared insensitive to pin prick, it was possible to elicit pain sensation (B, C, D, and E) using SDMS testing of the same dermatomal site at the same time.

It was also noted that, as the block progressed, a gradual increase in the strength of stimulus was required to induce B, C, D, and E until maximal stimuli on the dial produced just the feeling of sensation (B), and, finally, maximal stimulation resulted in no feeling of sensation (Level A). The time that was required to arrive at the latter case, particularly in the epidural group, was much longer than that expected and is commonly referred to as the block onset. In the same way, the regression time appeared much shorter than that expected.

A possible explanation of the above difference is that the pin prick of the skin is limited in producing a certain degree of noxious stimulation and also is inconsistent. On the other hand, the use of electric stimulation allowed the application of a gradual, consistent and a wider range of noxious stimulation that is possibly stimulating deeper tissue as well (sclerotome). Hard pricking of the skin was avoided in this study as this proved to be unhygienic and the pin could pierce the skin, producing damage and possible infection.

The establishment of full sensory block, as seen by the abscence of response following maximal stimulation delivered at a particular group of dermatomal sites, appeared to match that of the surgical stimulation. This appeared evident as none of the patients seemed to respond to surgical stimulation once the above was established. Also, when the depth of block started to regress below the required level and whereby evoked response (slight PGR response or slight EEG response) could be seen following maximal or near maximal stimulation, cardiovascular changes occurred in some patients while others complained of mild to strong sensation (in between B and C levels). At the same time anesthesia appeared adequate when it was tested with the pin prick method.

The above suggests that the SDMS can serve as both a dermatomal and sclerotomal monitor whereby stimulation of deeper tissue or deep pain below the skin level is possible through the use of a strong electric stimulus that penetrates the skin.

Repeated stimulation using a variable electrical stimulus produced consistent and reproducible subjective responses and/or evoked responses. These responses were varied when the patients were given sedation in the form of narcotics or tranquillizers. However, stimulation of the control (reference site) served as means of comparing both responses, i.e., that of control vs. tested dermatomal sites.

The time segment dermatome, which is defined as the spread of analgesia along the spinal segments over time and in response to a specific stimulus, appeared different according to the method that was used for the testing. The area of pain (time segment dermatome, sclerotome) in response to a lower level of stimulation (level B) appeared larger than that of pain in response to a stronger level of stimulation (D) and maximal stimulation. The area of the time segment dermatome of pain in response to pin prick testing appeared similar to that produced by electrical stimulation level of between that of B and D.

Using the pin prick method, the dermatomal area of hypothesia during the blocking process could not be quantified in terms of percentage of control. Using SDMS, it was possible to quantify these areas of hypothesia (reduced sensation) by superimposing the various time segment dermatomes one on top of the other to represent various levels of electric stimulation. In addition, through analysis of the magnitude of the evoked responses (PGR, EEG and EMG) and in response to that of control, the percentage of anesthesia could be estimated in relation to two points (for example, 0 and 100 where 0 represents normal sensation and 100 represents complete loss of sensation in response to a particular aximal stimulation). Therefore, the monitoring system and method of this invention can also be used in such a way where a baseline of the stimulus is noted as K 1 (which produces just a feeling of sensation, $1\frac{1}{2}$ (K 2), 2 (K 3) times as much as K 1.

Monitoring of the PGR following stimulation of the reference site at $C_3$ and $C_4$ using different strengths of stimuli representing B, C, D, and E, caused PGR waves that were different in magnitude when examined in the foot, chest wall and the hand and neck regions. Therefore, it is possible to monitor the sympathetic block by analyzing the physiological response such as the PGR and following the stimulation at a constant strength at the higher level (reference site). Changes in the sympathetic activity at various dermatomal sites can then be analyzed in terms of percentage of that of a control. Although the sympathetic block has always been regarded as an "all or none" block, the possibility of a differential sympathetic exists whereby the sympathetic depth of block at the particular dermatomal site (sympathotomal region) can be quantified.

As indicated in FIG. 19, the monitoring system 11 of this invention can be utilized as a part of an overall system for delivering an anesthetic to a patient. As shown in FIG. 19, the monitoring system 11 is positioned contiguous to the patient 17 in the same manner as described hereinabove with the output of physiological response detector 25 of monitoring system 11 being coupled to anesthetic control unit 65. Anesthetic control unit 65 supplies an output to anesthetic delivery unit 66, which output is indicative of a need for anesthetic by the patient (i.e., the monitoring system 11 indication is that the level and depth of anesthesia is not sufficient. Control unit 63 controls the application of the anesthetic to the patient by controlling anesthetic delivery unit 66, which unit may be a pump pumping anesthetic from a reservoir 67 to the patient through a catheter 69. A display indicating drug delivery is preferably displayed at drug information display 71 to facilitate control of such drug delivery, and the output from control unit 65 may also be utilized to trigger alarm circuit 73 which warns of stimulation termination and, through an output to anesthetic delivery unit 66, can also terminate automatic anesthetic delivery.

When utilized for drug delivery, the monitoring system thus controls anesthetic delivery to assure that anesthetic delivery is terminated when, or if, too much anesthetic is being delivered to the patient and also causes delivery of anesthetic to the patient when the monitoring system indicates that the level and depth of anesthetic is not sufficient for the intended purpose.

In view of the foregoing, it is to be realized that this invention provides a system and method for monitoring the sensory system of a patient to accurately and effectively enable determination of the level and depth of spinal and epidural nerve blocks affecting the sympathetic and motor nervous systems.

I claim:

1. An apparatus for determining sensory system pathway blocks related to preselected areas of the body of a patient by stimulating predetermined anatomical skin areas, said apparatus comprising:

a stimulating and sensing unit including stimulating means for stimulating peripheral receptors at said predetermined anatomical skin areas to thereby stimulate segmental associated pathways at the input side of the central nervous system so that the central nervous system can receive said stimulation from said peripheral receptors through unblocked ones of said segmental associated pathways and can receive no said stimulation from said peripheral receptors through blocked ones of said segmental associated pathways, said stimulating and sensing means also including sensing means receiving responses from the output side of the central nervous system, and said stimulating and sensing means having a plurality of elements and positioning means for adapting said elements to be positioned contiguous to the body of a patient along said predetermined anatomical skin areas so that, upon actuation of said stimulating means, a response can be detected at said sensing means, with respect to said unblocked ones of said segmental associated pathways, indicative of at least one predetermined physiological characteristic of said preselected areas of the body of the patient:

means for activating said stimulating means of said stimulating and sensing means;

response processing means connected with said sensing means of said stimulating and sensing means for receiving said responses from said sensing means and providing an output indicative of the interruption pattern at said preselected areas of the body of the patient as determined by said sensed blocked and unblocked pathways; and utilization means for receiving said output indicative of said interruption pattern from said response processing means and responsive thereto forming an indication thereof.

2. The apparatus of claim 1 wherein said plurality of elements are electrodes.

3. The apparatus of claim 2 wherein said positioning means non-invasively positions said electrodes contiguous to the body of a patient.

4. The apparatus of claim 1 wherein said stimulating and sensing means includes element selecting means for determining which of said plurality of elements is activated.

5. The apparatus of claim 4 wherein said activating means includes means for causing sequential activation of said plurality of elements.

6. The apparatus of claim 1 wherein said response processing means includes physiological response detecting means.

7. The apparatus of claim 1 wherein said utilization means includes display means connected with said response processing means for, displaying said output indicative of said interruption pattern.

8. An apparatus for determining sensory system pathway blocks, said apparatus comprising:

stimulating means having a plurality of elements and positioning means for adapting said elements to be positioned along predetermined anatomical skin areas of the body of a patient for stimulating peripheral receptors connected with segmental associated pathways of the input sensory system of the body of the patient when activated, said pathways of said input sensory system being connected with the central nervous system so that stimulation of said peripheral receptors causes stimulation of said central nervous system through unblocked ones of said segmental associated pathways with no stimulation of said central nervous system being caused through blocked ones of said segmental associated pathways;

element selecting means connected with said stimulating means for determining the selection of said plurality of elements to be activated;

sensing means having a portion to be positioned along said predetermined anatomical skin areas of the body of a patient for sensing a preselected physiological characteristic with respect to said unblocked ones of said segmental associated pathways responsive to stimulating of such a patient by said stimulating means, said sensing means including positioning means for adapting said portion to be positioned along said predetermined anatomical skin areas of the body of a patient;

physiological response detecting means connected with said sensing means for detecting said response sensed by said sensing means and providing an output indicative of the interruption pattern as determined by said sensed blocked and unblocked pathways; and utilization means for receiving said output from said physiological response detecting means and responsive thereto forming an indication of said interruption pattern.

9. The apparatus of claim 8 wherein said plurality of elements are electrodes, and wherein said stimulating means includes electronic means for stimulating the body of a patient through said electrodes.

10. The apparatus of claim 9 wherein said element selecting means includes automatic sequencing means for causing sequential activation of said electrodes.

11. The apparatus of claim 9 wherein said element selecting means includes manual means for activating said electrodes.

12. The apparatus of claim 8 wherein said element selecting means includes stimulator control means, pulse stimulating means controlled by said stimulator control means, element selector means, and element selector control means connected with said element selector means and said stimulator control means.

13. The apparatus of claim 8 wherein said sensing means are electrodes.

14. The apparatus of claim 8 wherein said utilization means includes display means connected with said physiological response detecting means for displaying said output therefrom indicative of said detected physiological responses.

15. The apparatus of claim 8 wherein said apparatus includes means for automatically terminating stimulation of said plurality of elements.

16. The apparatus of claim 15 wherein said stimulation terminating means includes reference means and comparator means connected with said reference means, said physiological response detecting means and said element selecting means, said comparator means comparing the outputs from said reference means and said physiological response means and terminating operation of said element selecting means when said output from said physiological reference means exceeds said output from said reference means.

17. The apparatus of claim 16 wherein said apparatus includes display means for indicating said termination of stimulation.

18. A method for determining sensory system pathway blocks at preselected areas of the body of a patient, said method comprising;

electrically stimulating peripheral receptors to thereby stimulate segmental associated pathways at the input side of the sensory system of the body of a patient leading to the central nervous system so that the central nervous system can receive said stimulation from said peripheral receptors through unblocked ones of said segmental associated pathways and can receive no said stimulation from said peripheral receptors through unblocked ones of said segmental associated pathways;

receiving responses from the output side of the central nervous system of the body of the patient with respect to unblocked ones of said segmental associated pathways that are indicative of a predetermined physiological characteristic of said preselected areas of the body of the patient; and determining from said sensed blocked and unblocked pathways the interruption pattern of pathway blocks at said preselected areas of the body of the patient.

19. The method of claim 18 wherein said step of stimulating peripheral receptors of the body of the patient includes sequentially and repeatedly stimulating said peripheral receptors of the body of the patient.

20. The method of claim 19 wherein said method includes progressively applying increasing levels of stimulation to said predetermined areas of the body of the patient.

21. The method of claim 19 wherein said method includes terminating sequential stimulation of said predetermined areas when a predetermined condition is sensed.

22. The method of claim 21 wherein said method includes comparing the received response with a reference to sense said predetermined condition.

23. The method of claim 18 wherein said method includes displaying an indication of said interruption pattern after determination of the same.

24. A method for continuously determining the extent of sensory and sympathetic blocks in the sensory system of the body of a patient, said method comprising:

sequentially and repeatedly stimulating peripheral receptors to thereby stimulate segmental associated pathways at the input side of the sensory system of the body of a patient leading to the central nervous system so that the central nervous system can receive said stimulation from said peripheral receptors through unblocked ones of said segmental associated pathways and can receive no said stimulation from said peripheral receptors through blocked ones of said segmental associated pathways;

monitoring the sensory system of the patient to sense responses with respect to unblocked ones of said segmental associated pathways that are indicative of at least one predetermined physiological characteristic to thereto provide an interruption pattern;

establishing a reference pattern for correlating said received response to said interruption pattern;

comparing said interruption pattern with said reference pattern to thereby continuously determine the extent of sensory and sympathetic blocks sensed to exist in the body of the patient; and utilizing said continuous determination to indicate the extent of sensory and sympathetic blocks.

25. The method of claim 24 wherein said method includes progressively increasing the level of stimulation at each of said predetermined areas.

26. The method of claim 24 wherein said step of monitoring the sensory system of the patient includes monitoring predetermined dermatomal sites of the body of the patient.

27. The method of claim 26 wherein said step of monitoring the sensory system of the patient includes selecting sensors capable of sensing at least phychogalvanic skin responses, and utilizing said sensors to sense at least phychogalvanic skin responses in response to said electrical stimulation of said predetermined dermatomal sites.

28. The method of claim 24 wherein said step of monitoring the sensory system of the patient includes sensing responses indicative of spinal and epidural nerve blocks as said predetermined physiological characteristic, and wherein said step of comparing includes determining the extent of spinal and epidural nerve blocks affecting the sympathetic and motor nervous system of the patient.

29. The method of claim 24 wherein said step of monitoring the sensory system of a patient includes sensing responses indicative of administered regional anesthetics as said predetermined physiological characteristic, and wherein said step of comparing includes determining the extent of regional anesthesia administered to a patient during surgery.

30. The method of claim 29 wherein said method includes providing an anesthetic administering means for administering anesthetics to a patient, and utilizing said determined extent of anesthesia of a patient to regulate the level and depth of anesthetic administered the patient.

* * * * *

UNITED STATES PATENT AND TRADEMARK OFFICE
CERTIFICATE OF CORRECTION

PATENT NO. : 4,570,640

DATED : February 18, 1986

INVENTOR(S) : Barsa

It is certified that error appears in the above-identified patent and that said Letters Patent is hereby corrected as shown below:

Column 8, line 21, change "group" to --groups--.

Column 14, line 49, after "exposing" insert --a--.

Column 20, line 14, change "SD$\underline{m}$S" to --SD$\underline{M}$S--.

Column 20, line 43, change "end" to --and--.

Column 21, line 26, change "on" to --one--.

Column 23, line 66, change "aximal" to --maximal--.

Column 27, line 3, "unblocked" should be --blocked--.

Column 28, line 5, change "response" to --responses--.

Column 28, line 46, change "level and depth" to --extent--.

Signed and Sealed this

Ninth Day of December, 1986

*Attest:*

DONALD J. QUIGG

*Attesting Officer*  *Commissioner of Patents and Trademarks*